(12) United States Patent
Gerrans et al.

(10) Patent No.: US 10,363,398 B2
(45) Date of Patent: Jul. 30, 2019

(54) STEERABLE CATHETER WITH FLEXING TIP MEMBER

(71) Applicants: Lawrence J. Gerrans, San Anselmo, CA (US); Erhan H. Gunday, Great Neck, NY (US); Alex Hsia, San Jose, CA (US); Jessie Tung, Cerritos, CA (US)

(72) Inventors: Lawrence J. Gerrans, San Anselmo, CA (US); Erhan H. Gunday, Great Neck, NY (US); Alex Hsia, San Jose, CA (US); Jessie Tung, Cerritos, CA (US)

(73) Assignee: Sanovas Intellectual Property, LLC, Reno, NV (US)

( * ) Notice: Subject to any disclaimer, the term of this patent is extended or adjusted under 35 U.S.C. 154(b) by 812 days.

(21) Appl. No.: 14/507,556

(22) Filed: Oct. 6, 2014

(65) Prior Publication Data

US 2016/0096004 A1    Apr. 7, 2016

(51) Int. Cl.
*A61B 1/00* (2006.01)
*A61M 25/01* (2006.01)
(Continued)

(52) U.S. Cl.
CPC ....... *A61M 25/0138* (2013.01); *A61B 1/0052* (2013.01); *A61B 1/0055* (2013.01); *A61B 1/0057* (2013.01); *A61B 1/00096* (2013.01); *A61B 1/00105* (2013.01); *A61B 1/045* (2013.01); *A61B 1/05* (2013.01);
(Continued)

(58) Field of Classification Search
CPC .......... A61M 25/0138; A61M 25/0053; A61M 25/0054; A61M 25/0147; A61B 1/051; A61B 1/0055; A61B 1/0676; A61B 1/045; A61B 1/0684; A61B 1/0057; A61B 1/053;
(Continued)

(56) References Cited

U.S. PATENT DOCUMENTS 4,580,551 A * 4/1986 Siegmund ............ A61B 1/0055 600/139
5,325,845 A * 7/1994 Adair ................... A61B 1/0055 600/114

(Continued)

FOREIGN PATENT DOCUMENTS

WO    9911313 A1    3/1999
WO    2013017875 A2    2/2013

*Primary Examiner* — Timothy J Neal
(74) *Attorney, Agent, or Firm* — Forge IP, PLLC

(57) ABSTRACT

A steerable catheter device includes a catheter body, a flexing tip member coupled to a distal end of the catheter body and having a wall with a first plurality of arcuate slits and a second plurality of arcuate slits, the first and second plurality of slits being diametrically opposed and alternating with each other, and an actuator that bends the flexing tip member, wherein at least a portion of the catheter body includes a braided sheath, and wherein each of the first and second plurality of slits has two ends and a center positioned midway between the two ends, and wherein all of the first plurality of slits have centers positioned along a first axis substantially parallel to the longitudinal axis of the catheter body and all of the second plurality of slits have centers positioned along a second axis substantially parallel to the longitudinal axis of the catheter body.

28 Claims, 20 Drawing Sheets

(51) Int. Cl.
   *A61B 1/005*   (2006.01)
   *A61B 1/06*   (2006.01)
   *A61B 1/045*   (2006.01)
   *A61B 1/05*   (2006.01)
   *A61M 25/00*   (2006.01)

(52) U.S. Cl.
   CPC .......... *A61B 1/0676* (2013.01); *A61B 1/0684* (2013.01); *A61M 25/0136* (2013.01); *A61M 25/005* (2013.01); *A61M 25/0069* (2013.01); *A61M 25/0147* (2013.01)

(58) Field of Classification Search
   CPC .............. A61B 1/00188; A61B 1/0019; A61B 1/00105
   USPC .......................................... 600/139, 141, 142
   See application file for complete search history.

(56) References Cited

U.S. PATENT DOCUMENTS

| | | | |
|---|---|---|---|
| 5,381,782 A | 1/1995 | DeLaRama et al. | |
| 5,741,429 A * | 4/1998 | Donadio, III | A61M 25/0043 216/10 |
| 6,117,071 A * | 9/2000 | Ito | A61B 1/00059 600/118 |
| 6,537,208 B1 * | 3/2003 | Konno | A61B 1/00188 348/340 |
| 6,579,246 B2 | 6/2003 | Jacobsen et al. | |
| 6,749,560 B1 * | 6/2004 | Konstorum | A61B 1/00071 600/139 |
| 6,780,151 B2 * | 8/2004 | Grabover | A61B 1/00071 600/141 |
| 7,090,637 B2 | 8/2006 | Danitz et al. | |
| 7,615,066 B2 | 11/2009 | Danitz et al. | |
| 7,637,903 B2 | 12/2009 | Lentz et al. | |
| 7,682,307 B2 | 3/2010 | Danitz et al. | |
| 8,092,444 B2 | 1/2012 | Lentz et al. | |
| 2003/0125757 A1 * | 7/2003 | Patel | A61B 17/320758 606/159 |
| 2004/0225186 A1 * | 11/2004 | Horne, Jr. | A61B 1/00071 600/139 |
| 2007/0071428 A1 * | 3/2007 | Chen | G02B 7/102 396/79 |
| 2007/0282358 A1 | 12/2007 | Remiszewski et al. | |
| 2009/0177040 A1 * | 7/2009 | Lyons | A61B 1/0055 600/141 |
| 2010/0312056 A1 * | 12/2010 | Galperin | A61B 1/0051 600/141 |
| 2011/0034769 A1 * | 2/2011 | Adair | H04N 5/3765 600/110 |
| 2011/0118610 A1 * | 5/2011 | Kuiper | A61B 1/0019 600/476 |
| 2013/0116549 A1 * | 5/2013 | Gunday | A61B 1/32 600/424 |
| 2013/0296649 A1 * | 11/2013 | Kirma | A61B 1/00177 600/109 |

\* cited by examiner

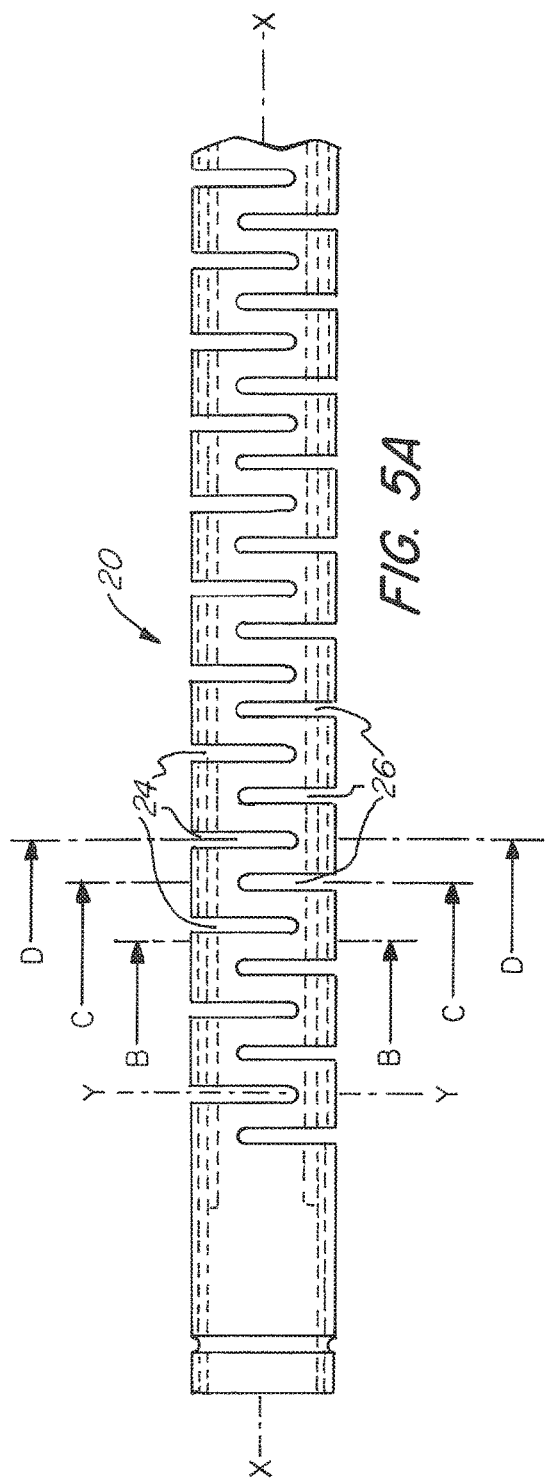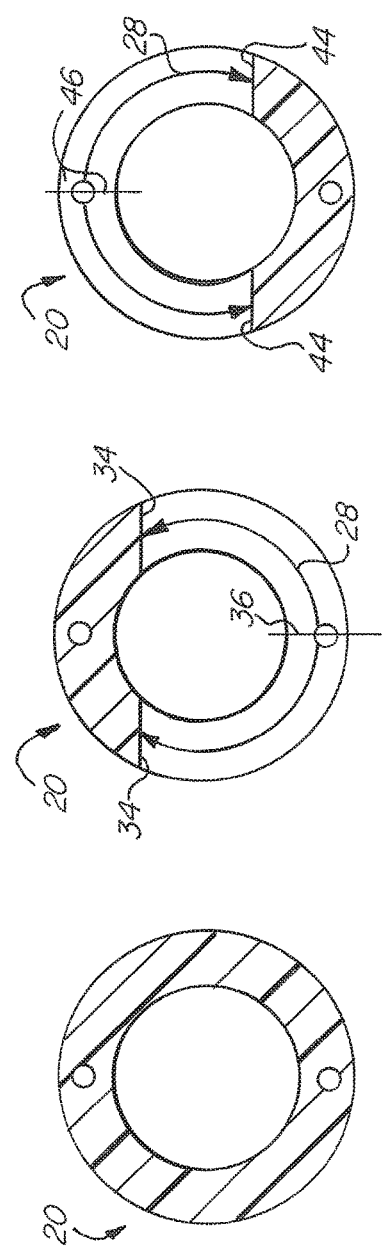
FIG. 5A
FIG. 5B
FIG. 5C
FIG. 5D

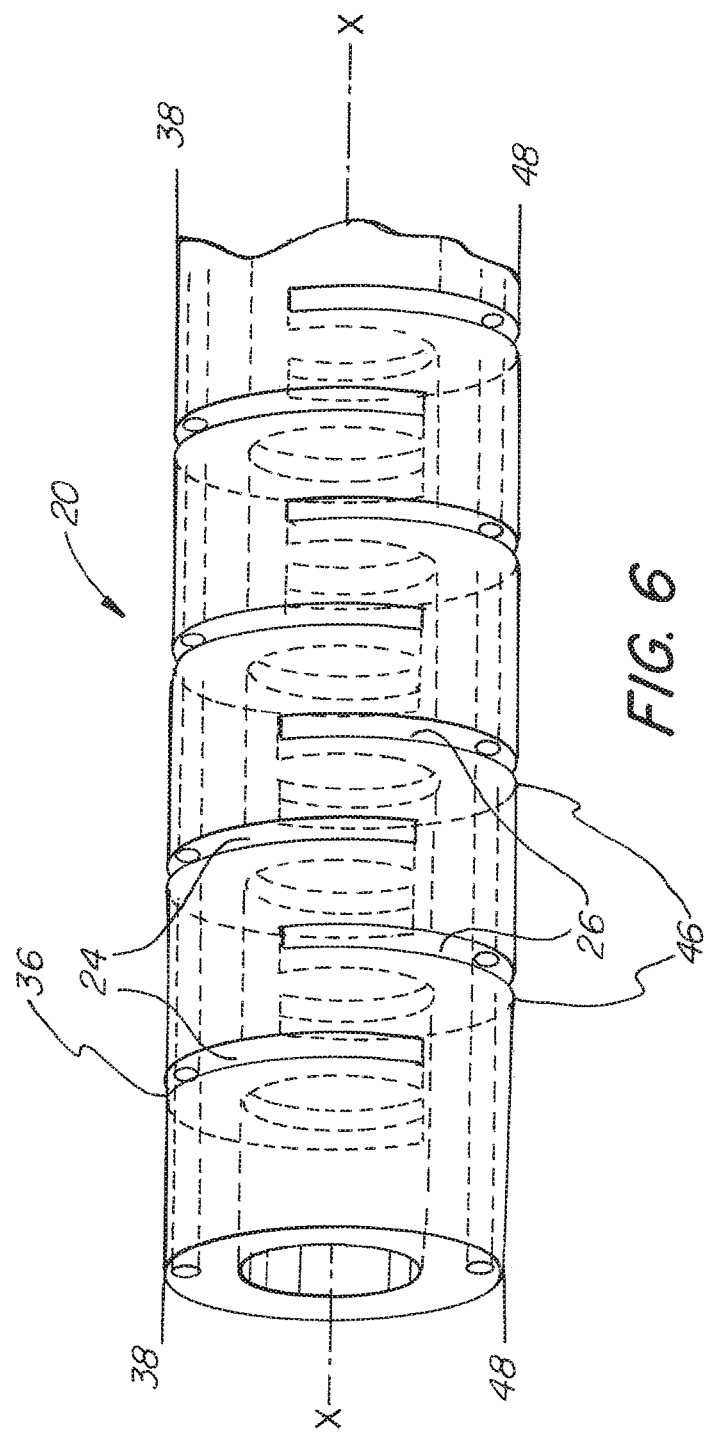

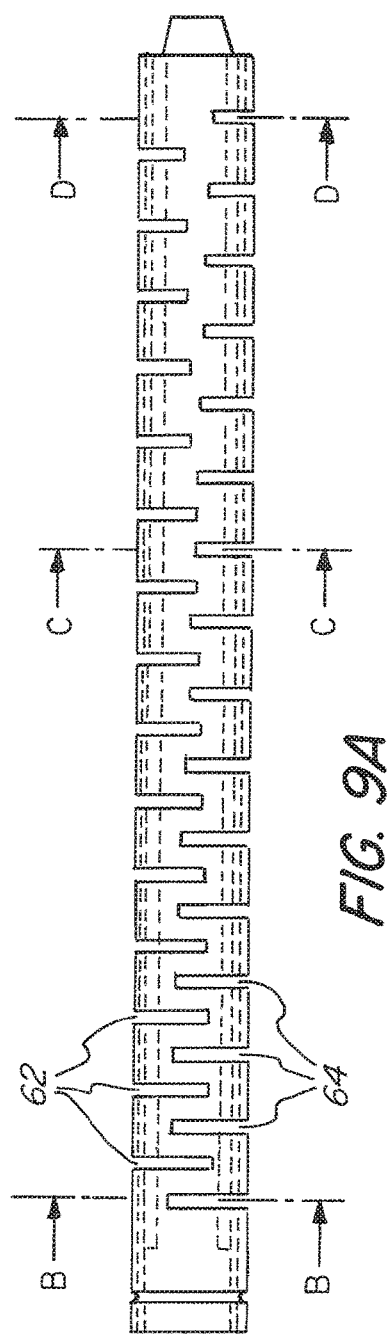
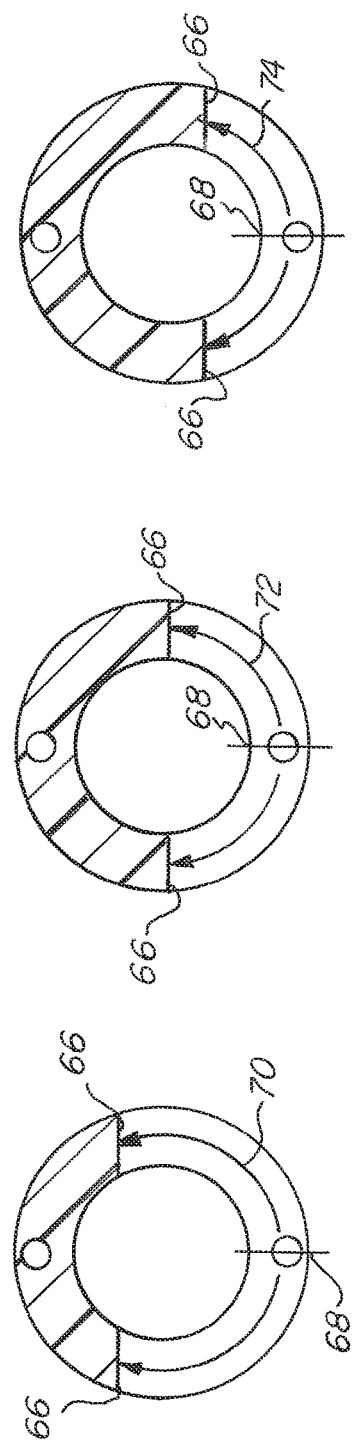
FIG. 9A
FIG. 9B
FIG. 9C
FIG. 9D

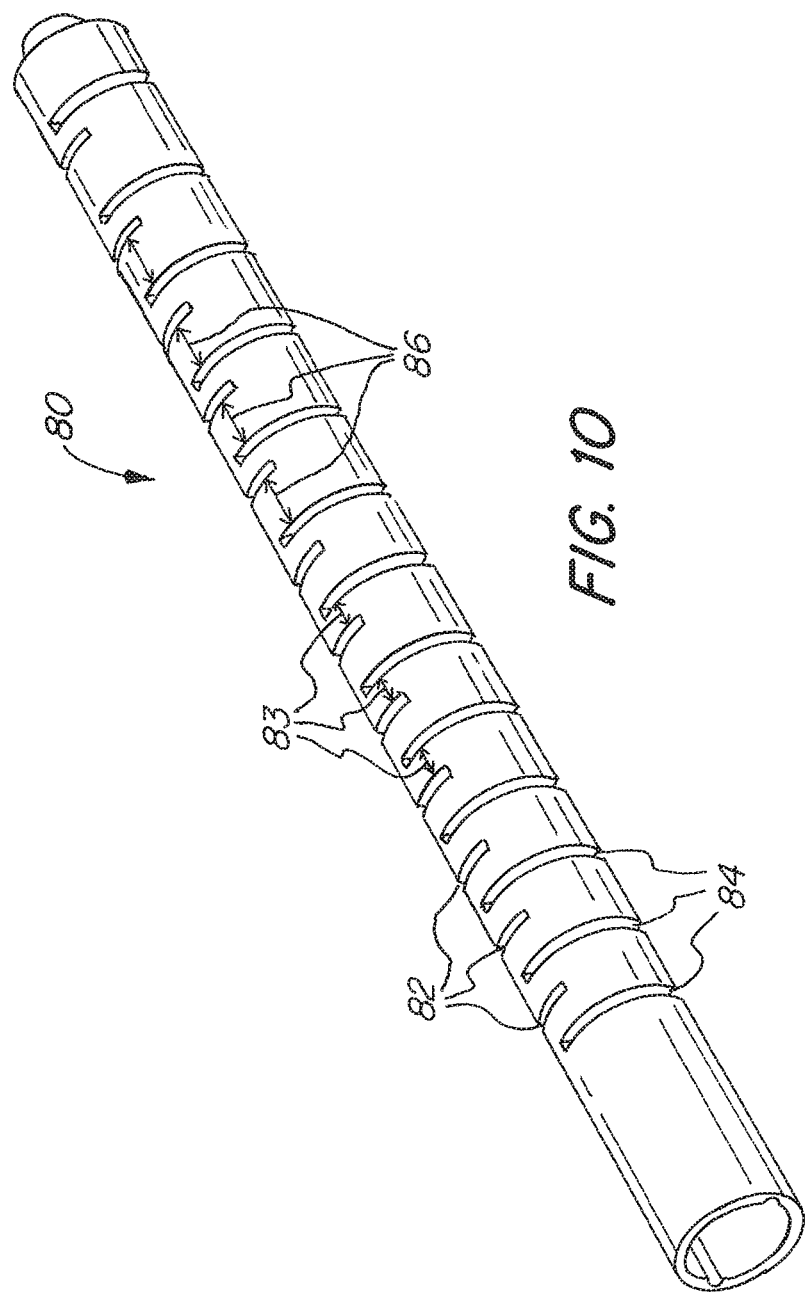

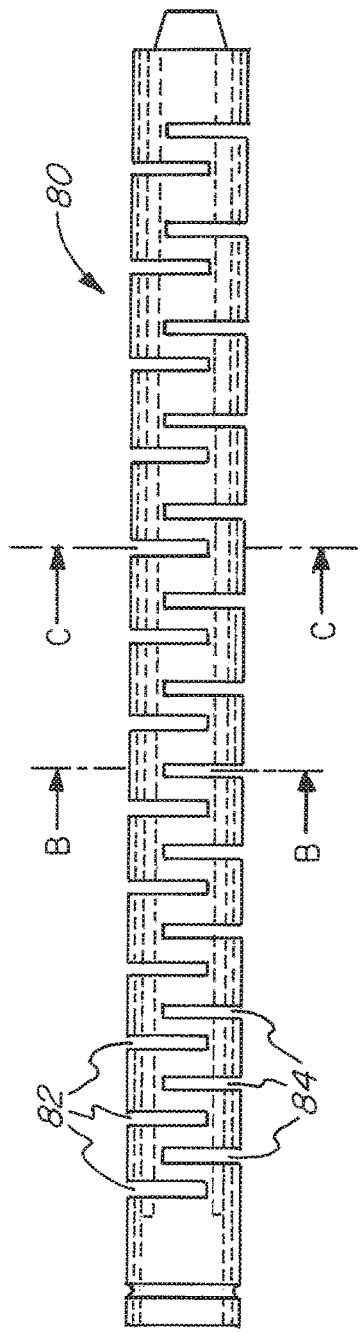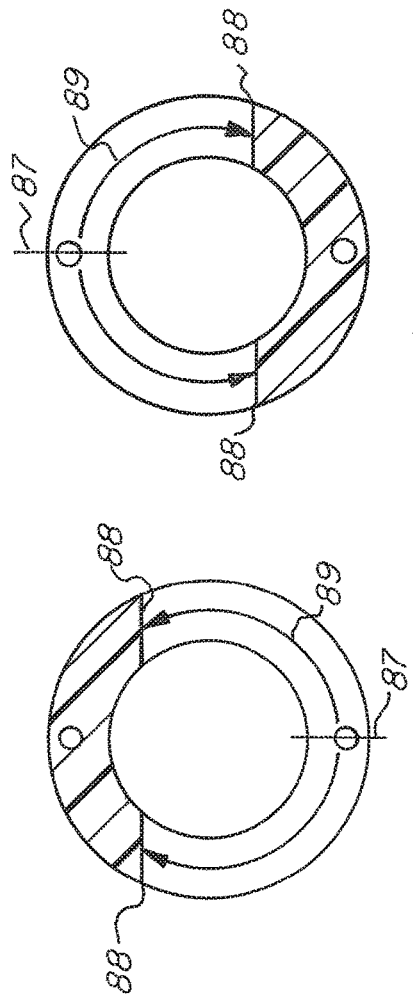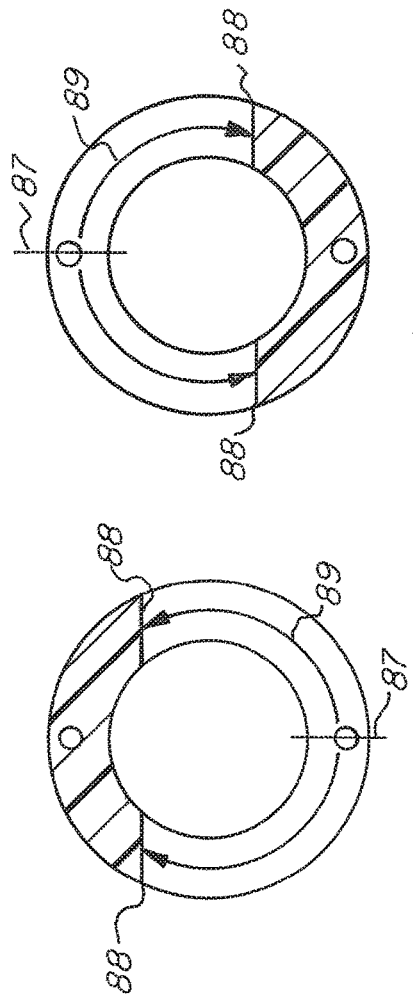

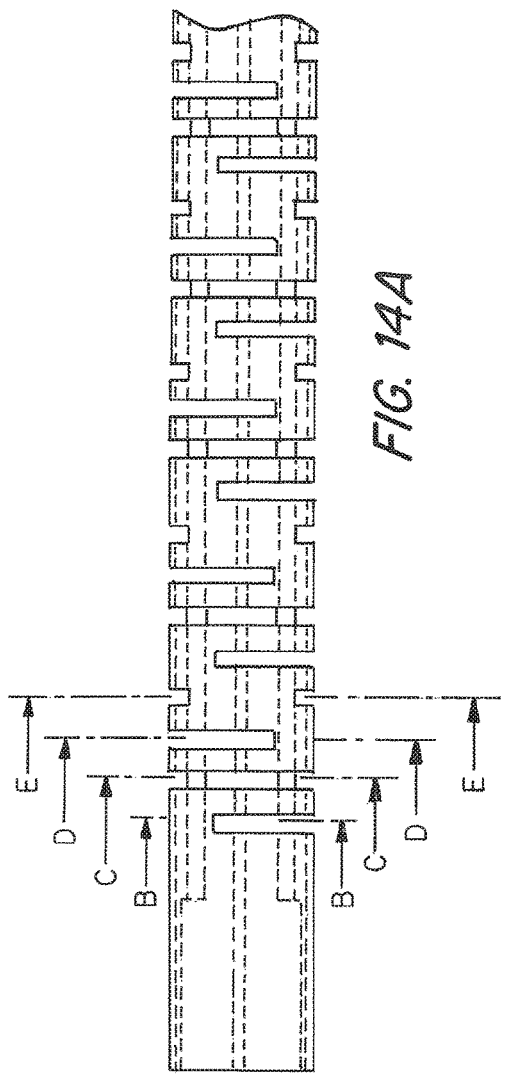
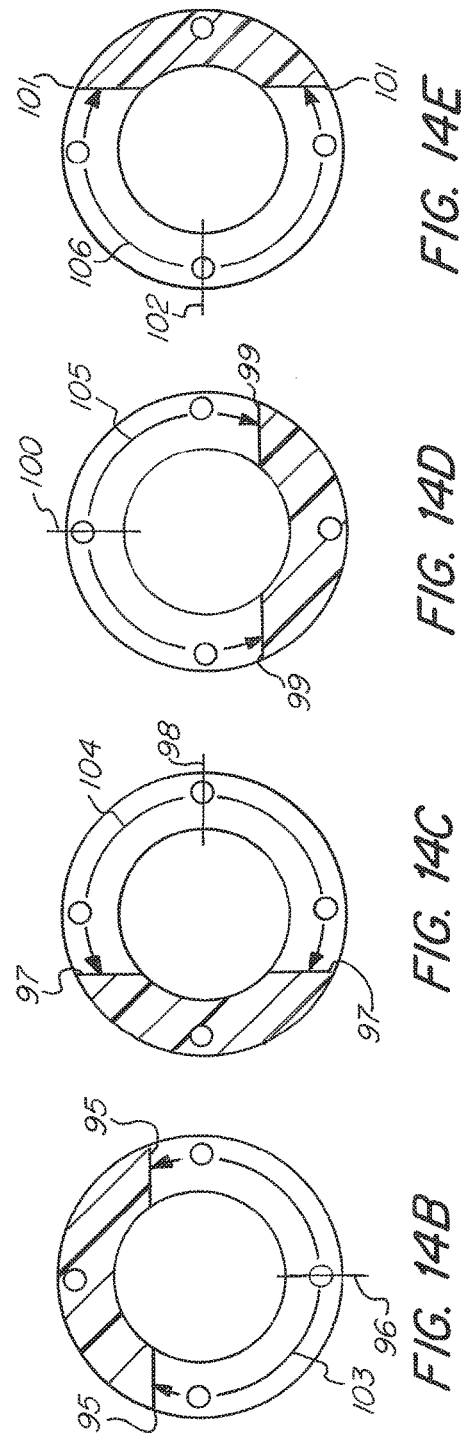

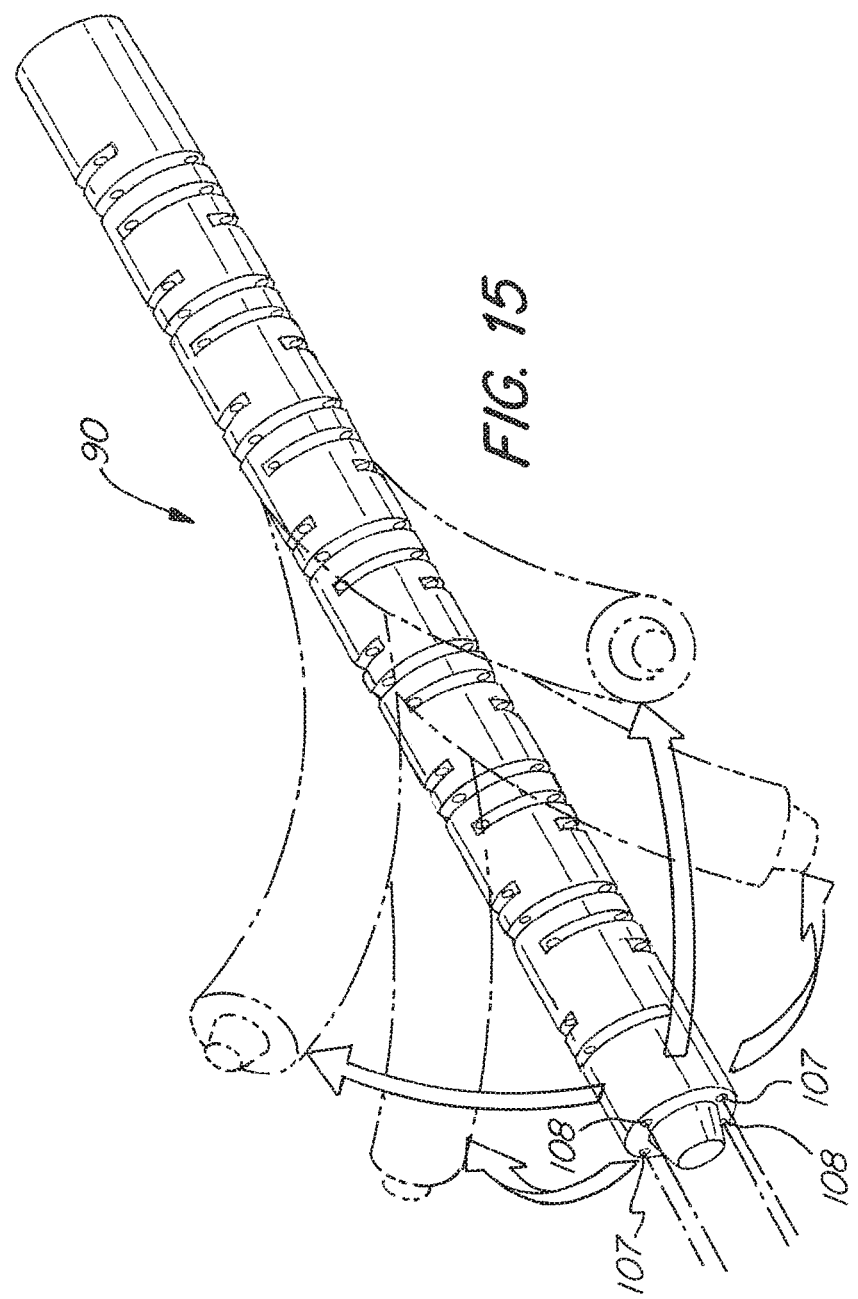

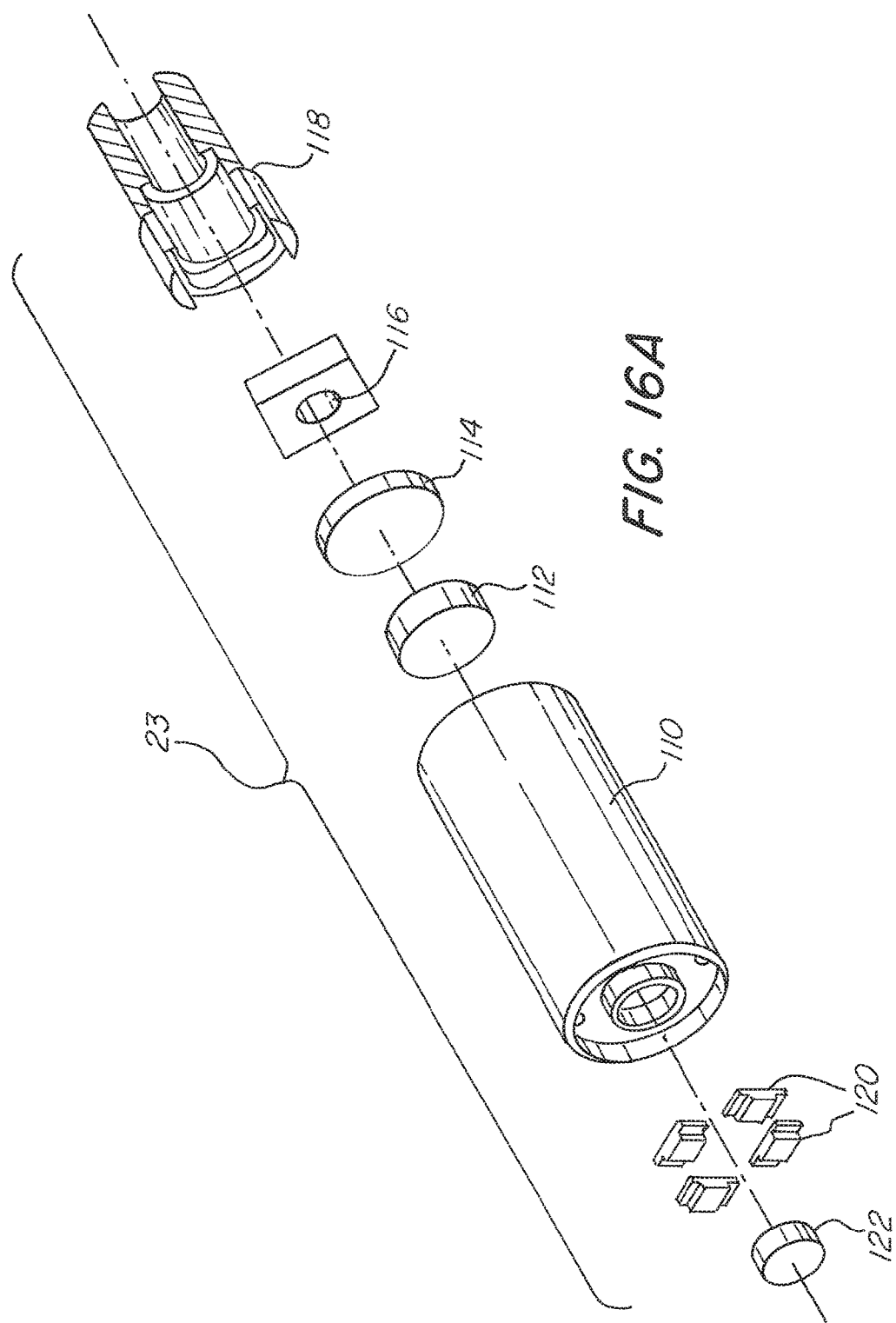

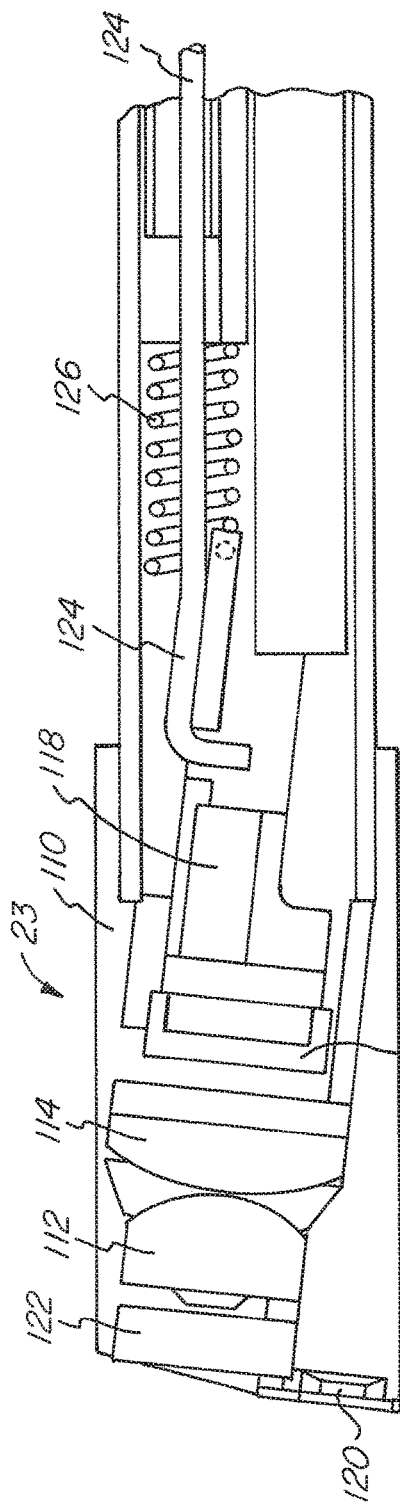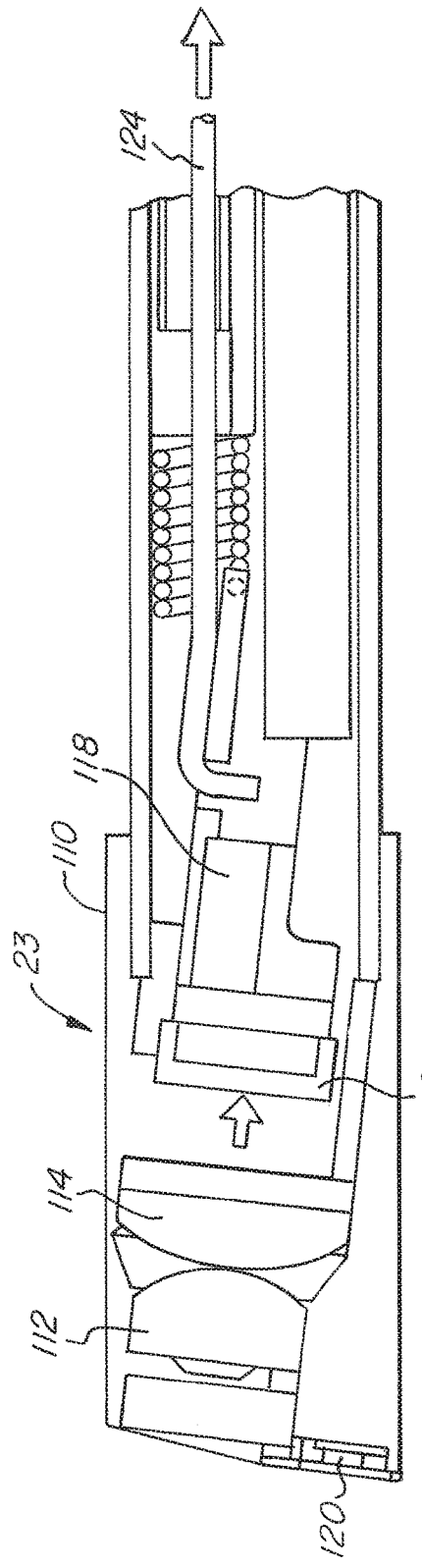
FIG. 17A
FIG. 17B

STEERABLE CATHETER WITH FLEXING TIP MEMBER

FIELD OF THE INVENTION

The present invention relates to systems and methods for moving a catheter in bodily cavities. More specifically, the present invention relates to a catheter having a flexing tip member, which allows the catheter to be steered.

BACKGROUND OF THE INVENTION

In general, catheters are used in medical procedures in which tubular structures, lumens, pleural cavities or spaces of the body, such as airways, vessels, organs and joints, are diagnostically examined and/or therapeutically treated. Catheters, which can be introduced into the body through a natural orifice or through an incision, can deliver imaging devices, surgical instruments, implants, fluids, drugs, pharmacologic materials, biologic materials, biologic agents and therapeutics to treat or remedy various pathologies found therein. Catheters also guide and deliver other components, such as guide wires, scaffolds and tools, to the intended site within the body.

Flexible, semi-rigid and rigid endoscopes are widely used in medicine to provide direct visualization for diagnostic and therapeutic purposes. Flexible, semi-rigid and rigid endoscopes are available in many sizes and configurations intended for use in different parts of the body and for a variety of diagnostic and therapeutic procedures. The visualization device (i.e., a fiber optic image bundle or a sensor at the distal tip of the device), together with the means for illumination, are an integral part of the endoscope. Endoscopes may also provide working channels to guide and deliver other instruments to the desired site. Endoscopes and endoscopic systems are, currently, a reusable and expensive resource in a physician's armamentarium. In addition, the endoscopic equipment systems required to operate endoscopes are often large, bulky and relatively immobile devices.

A limitation in the utility of the flexible endoscope is that their outer diameters are often too large, their inner 'working channel' diameters are often too small, and their lengths are often inadequate to appropriately diagnose and treat the anatomy and corresponding pathologies found in the far reaches of the body's organs, vessels and spaces. A further limitation of the utility of the flexible endoscope is that the articulation of the distal tip, and thus, its maneuverability, is typically accomplished by complicated mechanical structures that control the manipulating of the flexible endoscope's distal tip. As such, the maneuverability is limited by the capabilities of the mechanical structures. In addition, optimizing the external and internal diameters of the flexible endoscope is limited by the size and requirements of the mechanical structures.

There are several streerable catheter and guidewire devices known in the art. For example, U.S. Pat. No. 6,579,246 to Jacobsen et al. describes a guidewire system for introduction into bodily lumens having a distal section with a core wire with a tapering profile, with a coil disposed over the core wire, and a micromachined tube with a plurality of cuts coupled to the coil. The guide wire is maneuvered into bodily cavities by torque exerted on the proximal end of the wire, wherein the distal section with micromachined tubing is capable of bending away from the cavity walls. The International Publication No. WO 2013/017875 to Ataollahi et al. describes a catheter device having a steerable tip made with a plurality of stacked segments having a carbon fiber backbone and helical cuts therein. The streerable tip can be bent in a range of directions via guide tendons extending through the steerable tip. U.S. Pat. No. 7,637,903 to Lentz et al. describes a catheter having an articulation segment with tube having sections with variously oriented slits. The articulation segment allows for the catheter to coil in a plurality of directions and planes.

However, the steerable catheters described above suffer from a number of disadvantages. First, the structure of the known devices described above are still rather complex, requiring complicated mechanical structures to maneuver the devices. Additionally, while these known devices provide for means to bend sections of the catheter or guidewire body, they do not provide reinforced structures to avoid kinking of the catheter or guidewire body during insertion into bodily cavities. Furthermore, it is often desirable to be able to only bend the catheter tip in a single plane to provide for more precise maneuvering of the catheter. The devices described above are disadvantageous because, while they provide for articulation in a plurality of directions, it is not possible to limit the bending direction to only one plane.

What is desired, therefore, is a steerable catheter that can be steered through bodily cavities using a flexing tip member that provides a simple and accurate steering mechanism. What is also desired is a steerable catheter with a catheter body rigid enough to avoid kinking during insertion into body cavities, and that is able to make very tight turns with a short, steerable distal section and where the diameter of the catheter is as small as possible. What is also desired is a steerable catheter with an imaging device that is capable of providing a focused image regardless of how close the imaging device is positioned to target tissue. What is further desired is to have the above described catheter that can be manufactured at low cost as a disposable product.

SUMMARY OF THE INVENTION

Accordingly, it is an objective of the invention to provide a simple to use, lightweight, low cost, highly accurate, steerable catheter system where the catheter can be introduced into the body under direct and/or indirect visualization and can be made portable and disposable.

It is another objective of the invention to provide a steerable catheter that serves to eliminate the need to use complicated mechanical structures to articulate the distal tip of a catheter.

It is also an objective of the invention to provide a catheter having a sufficiently rigid body that provides needed torque and avoids kinking of the catheter during the insertion into bodily cavities.

It is a further objective of the present invention to provide a steerable catheter having a distal end that is able to bend at precise angles and planes so that the catheter can be maneuvered through very tight turns within the body, such as airway passages, vessel bifurcations, lumens, pleural cavities, and spaces within the tubular structures and capsular spaces of the body.

It is still another objective of the present invention to provide a steerable catheter where the maximum bend of the distal end of the catheter can be achieved with minimum pressures and forces.

It is a further objective of the present invention to use an imaging device used to help steer the catheter that is capable of providing a focused image regardless of how close the imaging device is positioned to target tissue.

In order to overcome the deficiencies of the prior art and to achieve at least some of the objectives and advantages listed, the invention comprises a steerable catheter device, including a catheter body having a proximal end, a distal end and a longitudinal axis, a flexing tip member coupled to the distal end of the catheter body and having a length, wherein the flexing tip member has a wall with a first plurality of arcuate slits and a second plurality of arcuate slits, wherein the first plurality of slits and the second plurality of slits are diametrically opposed, and wherein the first plurality of slits alternate with the second plurality of slits, and an actuator that bends the flexing tip member, wherein at least a portion of the catheter body includes a braided sheath, and wherein each of the first and second plurality of slits has two ends and a center positioned midway between the two ends and wherein all of the first plurality of slits have centers positioned along a first axis substantially parallel to the longitudinal axis of the catheter body and all of the second plurality of slits have centers positioned along a second axis substantially parallel to the longitudinal axis of the catheter body.

In some embodiments, the flexing tip member is removably coupled to the catheter body.

In certain embodiments, the slits are cut through the wall of the flexing tip member in a plane substantially perpendicular to the longitudinal axis of the catheter body.

In some advantageous embodiments, each of the first plurality of arcuate slits and each of the second plurality of arcuate slit have an arc length greater than 180 degrees.

In other advantageous embodiments, an arc length of the first plurality of slits and the second plurality of slits gradually changes along the length of the flexing tip member. In certain of these embodiments flexing tip member includes a first section, in which each of the first plurality of arcuate slits and each of the second plurality of arcuate slits has an arc length greater than 180 degrees, a second section, in which each of the first plurality of arcuate slits and each of the second plurality of arcuate slits has an arc length of about 180 degrees, and a third section, in which each of the first plurality of arcuate slits and each of the second plurality of arcuate slits has an arc length less than 180 degrees.

In some embodiments, a distance between adjacent slits is the same along the length of the flexing tip member. In additional embodiments, a distance between adjacent slits changes along the length of the flexing tip member.

In certain embodiments, the actuator includes at least two pull cables at least partially extending through the wall of the flexing tip member.

In some embodiments, the catheter device further includes an imaging device. In some of these embodiments, the imaging device is movably disposed in an inner lumen of the flexing tip member. In other of these embodiments, the imaging device is coupled to a distal end of the flexing tip member.

In some of the above embodiments, the imaging device includes a housing, at least one imaging sensor positioned in the housing, at least one lens positioned distally from said at least one imaging sensor, and at least one illumination device positioned adjacent the at least one imaging sensor. In certain of these embodiments, the imaging device further includes an actuator that moves the at least one imaging sensor relative the at least one lens. In additional of these embodiments, the imaging sensor is a CMOS sensor.

In certain embodiments, the at least one lens includes at least one positive lens. In some of these embodiments, the at least one lens includes two plano-convex lenses positioned distally from the imaging sensor.

In some cases, the illumination device is a LED.

In certain embodiments, the wall of the flexing tip member further includes a third plurality of arcuate slits and a fourth plurality of arcuate slits, wherein the third plurality of arcuate slits and the fourth plurality of arcuate slits are alternating and diametrically opposed, and wherein each of the third and fourth plurality of arcuate slits has two ends and a center positioned midway between the two ends, and wherein all of the third plurality of slits have centers positioned along a third axis substantially parallel to the longitudinal axis of the catheter body and radially offset at approximately 90 degree angle from the first axis, and all of the fourth plurality of arcuate slits have centers positioned along a fourth axis substantially parallel to the longitudinal axis of the catheter body and radially offset at approximately 90 degree angle from the second axis.

A steerable catheter device is also provided including a catheter body having a proximal end, a distal end and a longitudinal axis, a flexing tip member coupled to the distal end of the catheter body and having a length, wherein the flexing tip member comprises a wall with a first plurality of arcuate slits and a second plurality of arcuate slits, wherein the first and second plurality of slits are diametrically opposed, and wherein the first plurality of slits alternate with the second plurality of slits, an actuator that bends the flexing tip member, and an imaging device coupled to a distal end of the flexing tip member, wherein at least a portion of the catheter body comprises a braided sheath.

In some embodiments, each of the first and second plurality of slits has two ends and a center positioned midway between the two ends, and wherein all of the first plurality of slits have centers positioned along a first axis substantially parallel to the longitudinal axis of the catheter body and all of the second plurality of slits have centers positioned along a second axis substantially parallel to the longitudinal axis of the catheter body.

In certain embodiments, the actuator includes at least two pull cables at least partially extending through the wall of the flexing tip member.

In some embodiments, the imaging device includes a housing, at least one imaging sensor positioned in the housing, at least one lens positioned distally from the at least one imaging sensor, and at least one illumination device positioned adjacent the at least one imaging sensor. In certain of these embodiments, the imaging device further includes an actuator that moves the at least one imaging sensor relative the at least one lens. In additional of these embodiments, the imaging sensor is a CMOS sensor.

In some of the above embodiments, the at least one lens includes at least one positive lens. In certain of these embodiments, the at least one lens includes two plano-convex lenses positioned distally from the imaging sensor.

In some cases, the illumination device is a LED.

A method of orienting a catheter device within a bodily cavity is further provided, including the steps of positioning a catheter within a bodily cavity, the catheter having a catheter body with a proximal end, a distal end and a longitudinal axis, wherein at least a portion of the catheter body includes a braided sheath, a flexing tip member coupled to the distal end of the catheter body, wherein the flexing tip member has a wall with a first plurality of arcuate slits and a second plurality of arcuate slits, wherein the first and second plurality of arcuate slits are diametrically opposed, and wherein the first plurality of arcuate slits alternate with the second plurality of arcuate slits, and bending the flexing tip member in at least one direction, wherein each of the first and second plurality of slits has two ends and a center positioned midway between the two ends and wherein all of the first plurality of slits have centers positioned along a first axis substantially parallel to the longitudinal axis of the catheter body and all of the second plurality of slits have centers positioned along a second axis substantially parallel to the longitudinal axis of the catheter body.

In certain embodiments, the flexing tip member is removably coupled to the catheter body.

In some advantageous embodiments, each of the first plurality of arcuate slits and each of the second plurality of arcuate slit have an arc length greater than 180 degrees. In additional advantageous embodiments, an arc length of the first plurality of slits and the second plurality of slits gradually changes along the length of said flexing tip member.

In certain embodiments, a distance between adjacent slits is the same along the length of the flexing tip member. In additional embodiments, a distance between adjacent slits changes along the length of the flexing tip member.

In some cases, the step of bending the flexing tip member comprises pulling at least one cable at least partially extending through the wall of the flexing tip member.

In certain embodiments, the method further includes the step of viewing bodily tissue via an imaging device. In some of these embodiments, the imaging device is coupled to a distal end of the flexing tip member. In additional of these embodiments, the imaging device is movably disposed in an inner lumen of the flexing tip member.

In some of the above embodiments, the imaging device includes at least one lens and at least one imaging sensor. In certain of these embodiments, the method further includes the step of moving the at least one imaging sensor relative the at least one lens.

In certain embodiments, the method also includes the step of illuminating bodily tissue via at least one illumination device.

In some cases, the step of bending the flexing tip member includes moving the flexing tip in at least one of a first plane and a second plane, wherein the first and second planes are substantially parallel to the longitudinal axis of the catheter body and substantially perpendicular to one another.

Other objects of the invention and its particular features and advantages will become more apparent from consideration of the following drawings and accompanying detailed description.

BRIEF DESCRIPTION OF THE DRAWINGS

FIG. 5A is a side view of the flexing tip member of FIG. 4.

FIG. 5B is a cross-sectional view of the flexing tip member of FIG. 5A, taken along the line "B-B".

FIG. 5C is a cross-sectional view of the flexing tip member of FIG. 5A, taken along the line "C-C".

FIG. 5D is a cross-sectional view of the flexing tip member of FIG. 5A, taken along the line "D-D".

FIG. 6 is an isometric view of the flexing tip member of FIG. 4.

FIG. 9A is a side view of the flexing tip member of FIG. 8.

FIG. 9B is a cross-sectional view of the flexing tip member of FIG. 9A, taken along the line "B-B".

FIG. 9C is a cross-sectional view of the flexing tip member of FIG. 9A, taken along the line "C-C".

FIG. 9D is a cross-sectional view of the flexing tip member of FIG. 9A, taken along the line "D-D".

FIG. 10 is a perspective view of the flexing tip member of the catheter device of FIG. 1, with slits positioned at a different distance.

FIG. 11A is a side view of the flexing tip member of FIG. 10.

FIG. 11B is a cross-sectional view of the flexing tip member of FIG. 11A, taken along the line "B-B".

FIG. 11C is a cross-sectional view of the flexing tip member of FIG. 11A, taken along the line "C-C".

FIG. 14A is a side view of the flexing tip member of FIG. 12.

FIG. 14B is a cross-sectional view of the flexing tip member of FIG. 14A, taken along the line "B-B".

FIG. 14C is a cross-sectional view of the flexing tip member of FIG. 14A, taken along the line "C-C".

FIG. 14D is a cross-sectional view of the flexing tip member of FIG. 14A, taken along the line "D-D".

FIG. 14E is a cross-sectional view of the flexing tip member of FIG. 14A, taken along the line "E-E".

FIG. 15 is a perspective view of the flexing tip member of FIG. 12, showing actuation of the member.

FIG. 16A is an exploded perspective view of an imaging device of the catheter device of FIG. 1.

FIGS. 17A and 17B are exposed side views of the distal end of the catheter device of FIG. 1 with the attached imaging device, showing actuation of the imaging device.

DETAILED DESCRIPTION OF THE INVENTION

Figure 1:
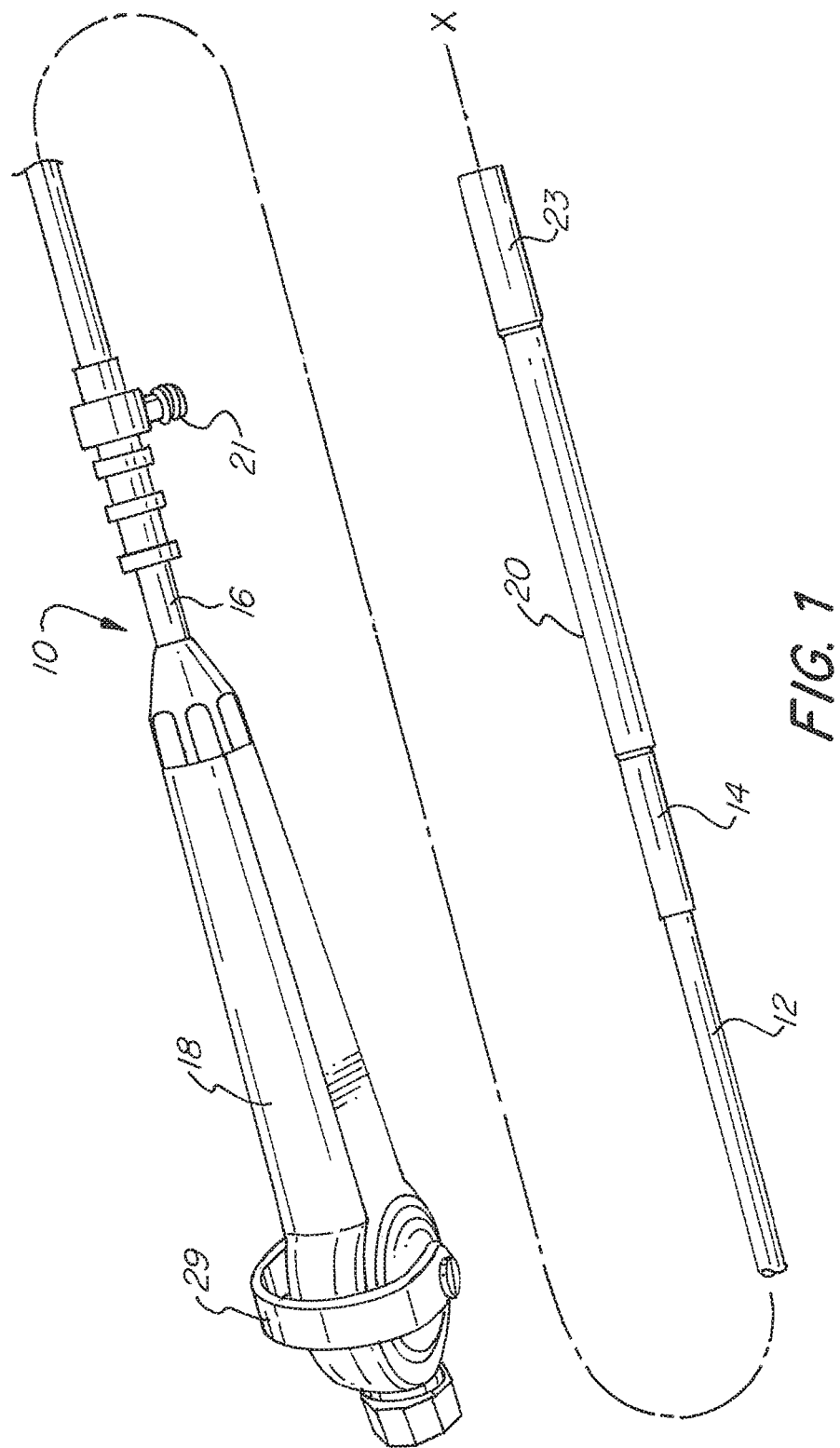
FIG. 1 is an exploded isometric view of the catheter device in accordance with the present invention.

The basic components of one embodiment of a steerable catheter device in accordance with the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

As shown in FIG. 1, a steerable catheter, generally indicated at reference character (10), includes an elongated catheter body (12) having a proximal end (16) and a distal end (14). The catheter body (12) has a generally cylindrical body with an inner lumen. The catheter body (12) has a longitudinal axis (X-X) along which the length of the catheter body is defined.

The elongated catheter body (12) may be constructed from any suitable rigid or semi-rigid material, such as, for example, polyether amide (PEBA), Pebax® or polyurethane. The outer diameter of the catheter should usually be made as small as possible. Typically, the outer diameter is less than about 3 mm. Preferably, the outer diameter of the catheter body is less than 2 mm. The inner lumen should be as large as possible to easily pass various medical or drug delivery instruments. In certain advantageous embodiments of the invention, the inner lumen has a diameter of at least about 1.2 mm.

In certain advantageous embodiments, the catheter body (12) includes imaging markers, such as radio opaque rings, located throughout the length of, or at or near, the distal end (14). Such markers can be selected and appropriately positioned in order to reflect the relevant waves of various imaging modalities (e.g., x-ray) in order to allow the use of such modalities to assist with the precise positioning of the catheter. In another advantageous embodiment, a braided sheath discussed further below is radiopaque.

The inner lumen of the catheter body (12) may be used to deploy various instruments, devices, or fluids into the desired part of the airway, vessel, lumen, or pleural cavity of or other bodily cavity, such as an imaging device, an instrument, a device, or a fluid. The proximal end (16) of the catheter body (12) may include one or more ports (21) for introduction of various things into the catheter lumen. The inner lumen of the catheter may further be divided into a plurality of lumens (not shown), through which an imaging device, an instrument, a device, or a fluid may be placed. The inner lumen(s) can be used to deliver any number of things to assist with opening the cavity, circulation, aspiration, respiration, the decomposition of an obstruction, or the stimulation of healing in the affected area, including air, aspirates, drugs, biologics, biogenetic agents, nano-particulates, solutions, stem cell and gene therapies, and stents and scaffolds. Specifically, the catheter device (10) could be used for the deployment of pro-generative vehicles and/or catalysts in the repair, treatment, and therapy of the targeted areas, including biologic, nano-particulate materials and/or biogenetic materials, structures, scaffolds, and similar devices and vehicles, including, for example, bone morphogenetic proteins, microcrystalline nano-particulates, collagens, de-mineralized bone chips, calcium-based structures, poly glycolic acids, poly lactic acids, and hyaluronic acids. The catheter device (10) can likewise be used for the deployment of inert, inelastic, and semi-rigid materials, such as, for example, PEEK, ceramic, cobalt chrome, titanium, and stainless steel.

Figure 2:
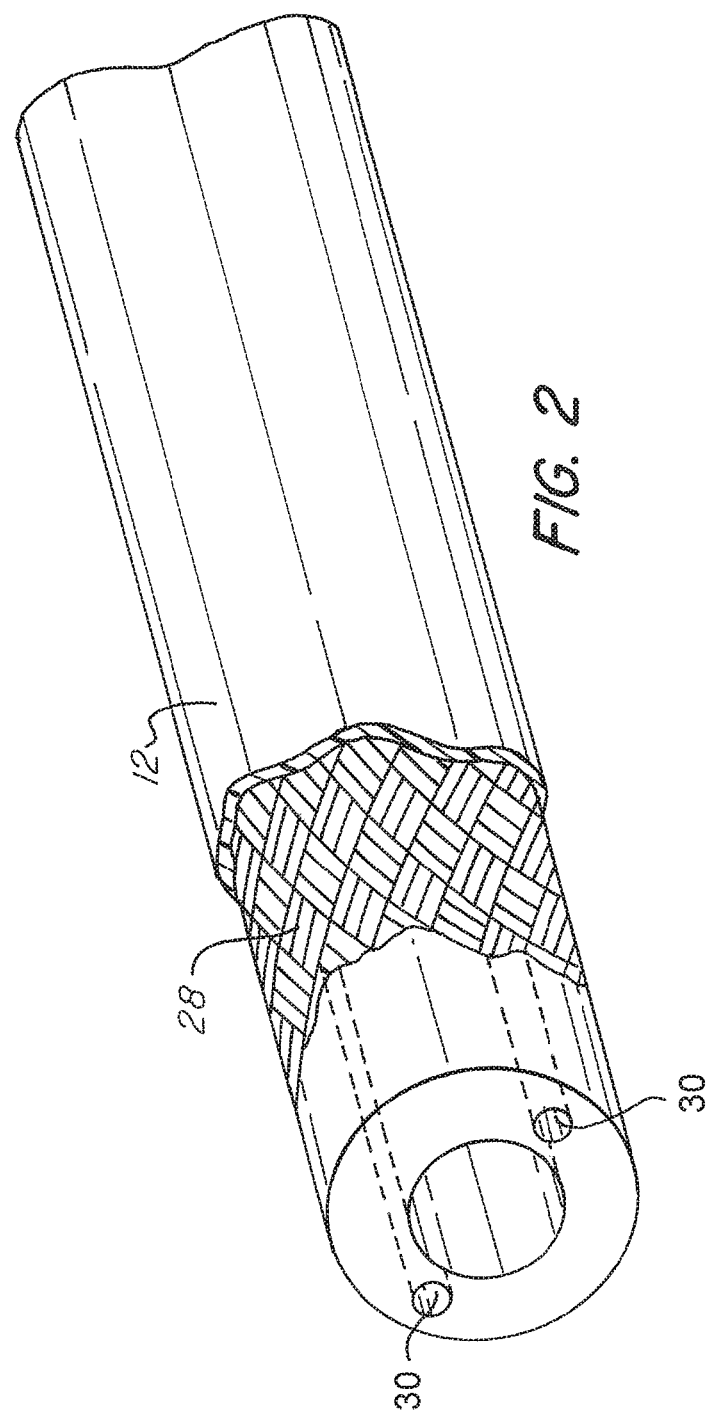
FIG. 2 is a partially exposed view of the catheter body of the catheter device of FIG. 1.

In an advantageous embodiment of the present invention, at least a portion of the elongated body (12) of the catheter device (10) has a braided sheath to assist the bending motion of the catheter body and distal tip. As shown in FIG. 2, the braided sheath (28) has a generally cylindrical shape and is made with any suitable material, such as, for example, metal or plastic filaments, that are weaved together via any suitable method. The braided sheath (28) prevents the catheter body from kinking and provides an improved torque while not requiring increased thickness of the catheter body (12), so that the catheter outer diameter may be kept smaller. The sheath (28) allows the distal tip (14) of the catheter device (10) to be stiffer and stay straight while the catheter is being pushed through the body vessel. The braided sheath (28) can be molded over during the catheter extrusion process and can run the entire length of the catheter body (12). Alternatively, the distal tip (14) and/or catheter body (12), may be molded or extruded in a first step and the braided sheath (28) may be disposed within the inner lumen.

The catheter device (10) also includes a flexing tip member (20) coupled to the distal end (14) of the catheter body (12). In the exemplary embodiment shown in FIG. 1, the flexing tip member (20) is covered by a shrink wrap which provides a smooth outer surface to facilitate easy insertion and maneuvering of the catheter inside bodily cavities. The shrink wrap may be removed and the flexing tip member (20) may be disconnected from the catheter body (12) and replaced with a new tip member, if desirable. This is advantageous because it avoids the expense of replacing the entire catheter device (10) in case of wear out/damage of the flexing tip member or if a different tip member having different optical or flexing characteristics is desirable for a particular medical procedure.

The catheter device (10) further includes an actuator (18) positioned at the proximal end (16) of the catheter body (12). The actuator (18) enables bending of the flexing tip member (20), as further described below. It is understood that the actuator shown in the figures is only exemplary, and that any other suitable actuator may be used in accordance with the present invention.

Figure 3:
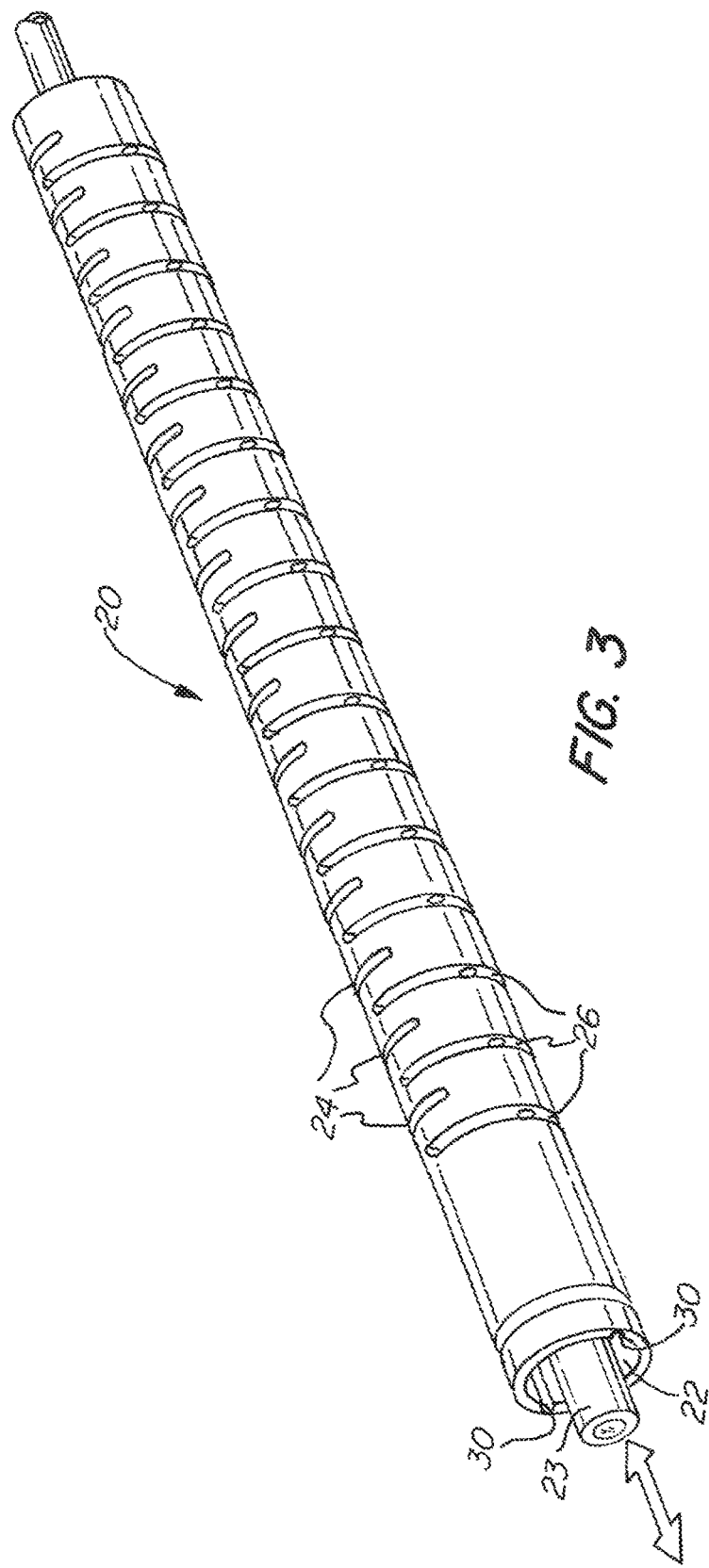
FIG. 3 is a perspective view of a flexing tip member of the catheter device of FIG. 1.
Figure 4:
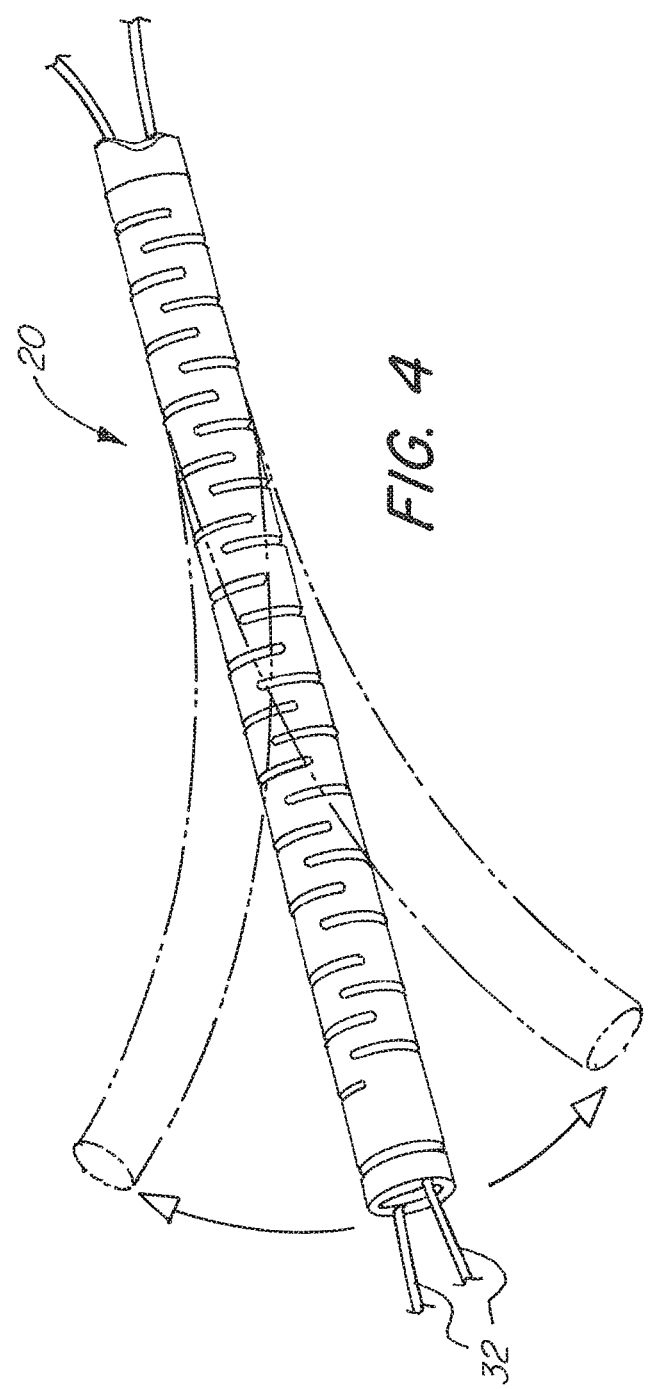
FIG. 4 is a perspective view of the flexing tip member of FIG. 3.

One exemplary embodiment of the flexing tip member (20) is illustrated in FIG. 3. The flexing tip member (20) has a generally cylindrical body with an inner lumen (22). The body is made with any suitable material that has desired flexibility, for example, a polymer plastic such as PEEK, and may be made by any suitable manufacturing method, such as, for example, extrusion. In the embodiment shown in this figure, the flexing tip member (20) has a first plurality of arcuate slits (24) and a second plurality of arcuate slits (26). The slits are cut through the wall of the flexing tip member (20) by any suitable method, such as mechanical or laser cutting. The flexing tip member further includes at least two channels (30) that accommodate pull wires (32) for actuation of the flexible tip member, as shown in FIG. 4.

As shown in this figure, the first plurality of slits (24) and the second plurality of slits (26) are diametrically opposed, and a distance between adjacent slits is the same along the length of the flexing tip member (20). This provides for a more accurate control of the movement of the flexing tip member, such that it only moves in one plane, as shown in FIG. 4. This is advantageous when the catheter device (10) is used in very small bodily cavities wherein it is crucial to be able to precisely control the movement of the catheter tip to facilitate the introduction of the catheter inside the cavity. It is understood, however, that the first and second pluralities of slits can be positioned at a different orientation with respect to each other, depending on the desired degree and direction of movement of the flexing tip member (20).

Additionally, in the embodiment shown in FIG. 3, the first plurality of slits (24) alternate with said second plurality of slits (26). This allows for uniform bending of the flexing tip member (20) in both directions. Again, it is understood that the first and second plurality of slits may not alternate along the entire length of the flexing tip member. For example, the flexing tip member (20) may have sections with only the first plurality of slits or only the second plurality of slits to allow for a larger degree of bending of the tip in one direction.

Referring to FIGS. 5A-5D, the first and second pluralities of slits are cut in a plane Y-Y substantially perpendicular to the longitudinal axis X-X of the catheter body. In other advantageous embodiments, some or all of the slits may be cut in a plane positioned at less than a 90 degree angle to the longitudinal axis of the catheter body to alter the bending characteristics of the flexing member (20). Each of the first and second plurality of slits (24, 26) extends through the entire thickness of the wall of the flexing tip member (20). As shown in FIGS. 5C and 5D, each of the first plurality of slits (24) has two ends (34) and a center (36) positioned midway between the two ends, and each of the second plurality of slits (26) has two ends (44) and a center (46) positioned midway between the two ends. Each of the slits has an arc length (28) measured along the circumference of the flexing tip member (20) and extending from one end to the other end of each slit. In the embodiment shown in these figures, the arc length (28) of each of the first and second plurality of slits (24, 26) is greater than 180 degrees, as can be seen in FIGS. 5C and 5D. In other embodiments, as described in more detail below, some or all of the slits may have an arc length of about 180 degrees or less than 180 degrees.

As illustrated in FIG. 6, all of the first plurality of slits (24) have their centers (36) positioned along a first axis (38) substantially parallel to the longitudinal axis (X-X) of the catheter body. Similarly, all of the second plurality of slits (26) have their centers (46) positioned along a second axis (48) substantially parallel to the longitudinal axis (X-X) of the catheter body. This design facilitates more precise control of the movement of the flexing tip member, such that it only moves in one plane, which can be advantageous when the catheter device (10) is used in very small bodily cavities.

Figure 7:
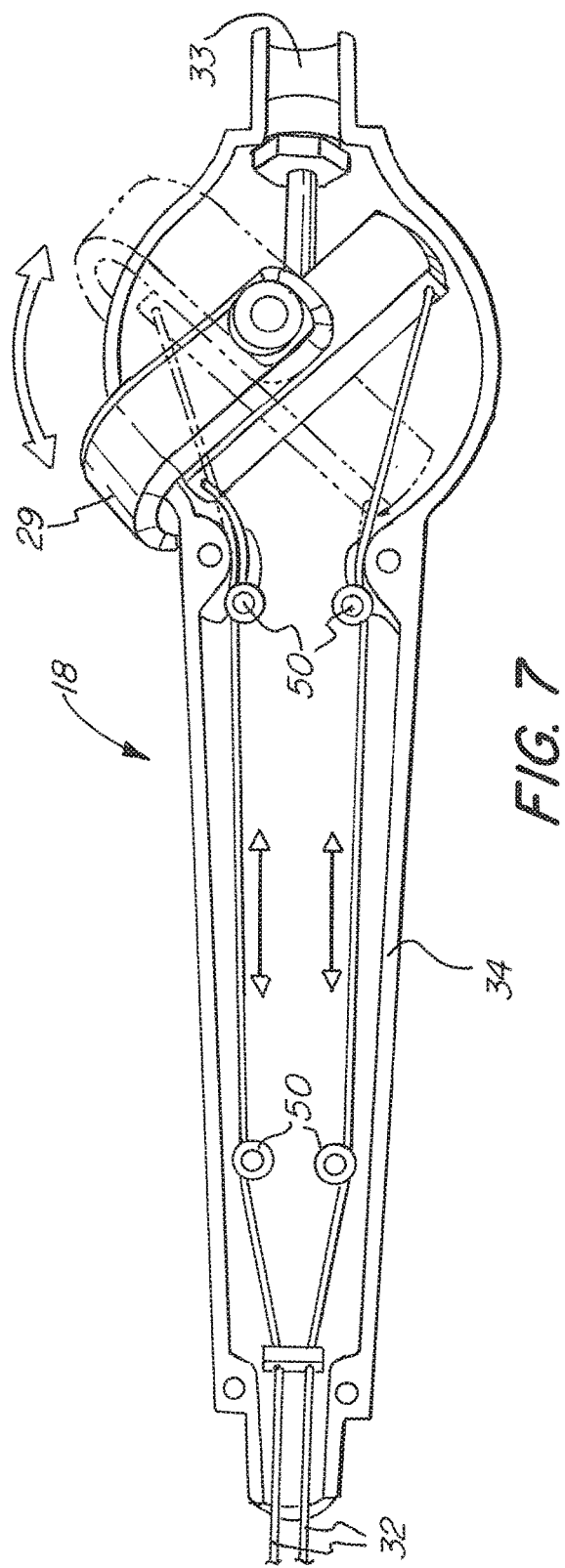
FIG. 7 is an exposed side view of an actuator of the catheter device of FIG. 1.

FIG. 7 illustrates the actuator (18) positioned at the proximal end of the catheter body. The actuator (18) includes a housing (31) made with any suitable material, such as plastic. The housing has a thumb control member (29) positioned at its proximal end that moves between two positions, as shown in this figure. The thumb control member (29) is coupled to ends of two pull cables (32) that at least partially extend through the catheter body (12) and through the flexing tip member (20). The opposite ends of the pull cables (32), shown in FIG. 4, are coupled to the distal end of the flexing tip member (20) in any of various ways. For example, the ends may be glued to the tip of the member (20). Alternatively, a single pull cable may be used, extending down the channel (30) and loop at the tip into the opposite channel (30). The actuator housing (31) includes two or more guides (50) for guiding the pull cables (32). It is noted that other devices, such as imaging device optic cables, may be extended through the actuator housing (31), if necessary. The housing (31) may have a port (33) at its proximal end for introduction of various devices.

By moving the thumb control member (29) from one position to the other, one of the pull cables (32) is coiled in a proximal direction, causing the flexing tip member (20) to bend in one direction. When the thumb control member (29) is moved in the opposite direction, the second pull cable (32) is coiled in the proximal direction causing the flexing tip member (20) to bend in the opposite direction. The degree of bending of the flexing tip member (20) is controlled by how far the thumb control member (29) is moved between the two positions. This actuator design is simple and efficient as it only requires a physician to move his or her thumb to actuate the catheter. However, it is understood any other suitable actuator may be used to bend the flexing tip member (20) in accordance with the present invention.

Another exemplary embodiment of the flexing tip member is illustrated in FIGS. 8 and 9A-9D. Similarly to the embodiment described above in connection with FIGS. 3-6, the flexing tip member (60) has a first plurality of arcuate slits (62) and a second plurality of arcuate slits (64). The first and second pluralities of slits (62, 64) are diametrically opposed, and the first plurality of slits (62) alternate with the second plurality of slits (64). A distance between adjacent slits is the same along the length of the flexing tip member (60). Each of the slits has two ends (66) and a center (68) and an arc length extending between the two ends of each slit. All of the first plurality of slits (62) have their centers positioned along a first axis substantially parallel to the longitudinal axis of the catheter body, and all of the second plurality of slits (64) have their centers positioned along a second axis substantially parallel to the longitudinal axis of the catheter body.

Figure 8:
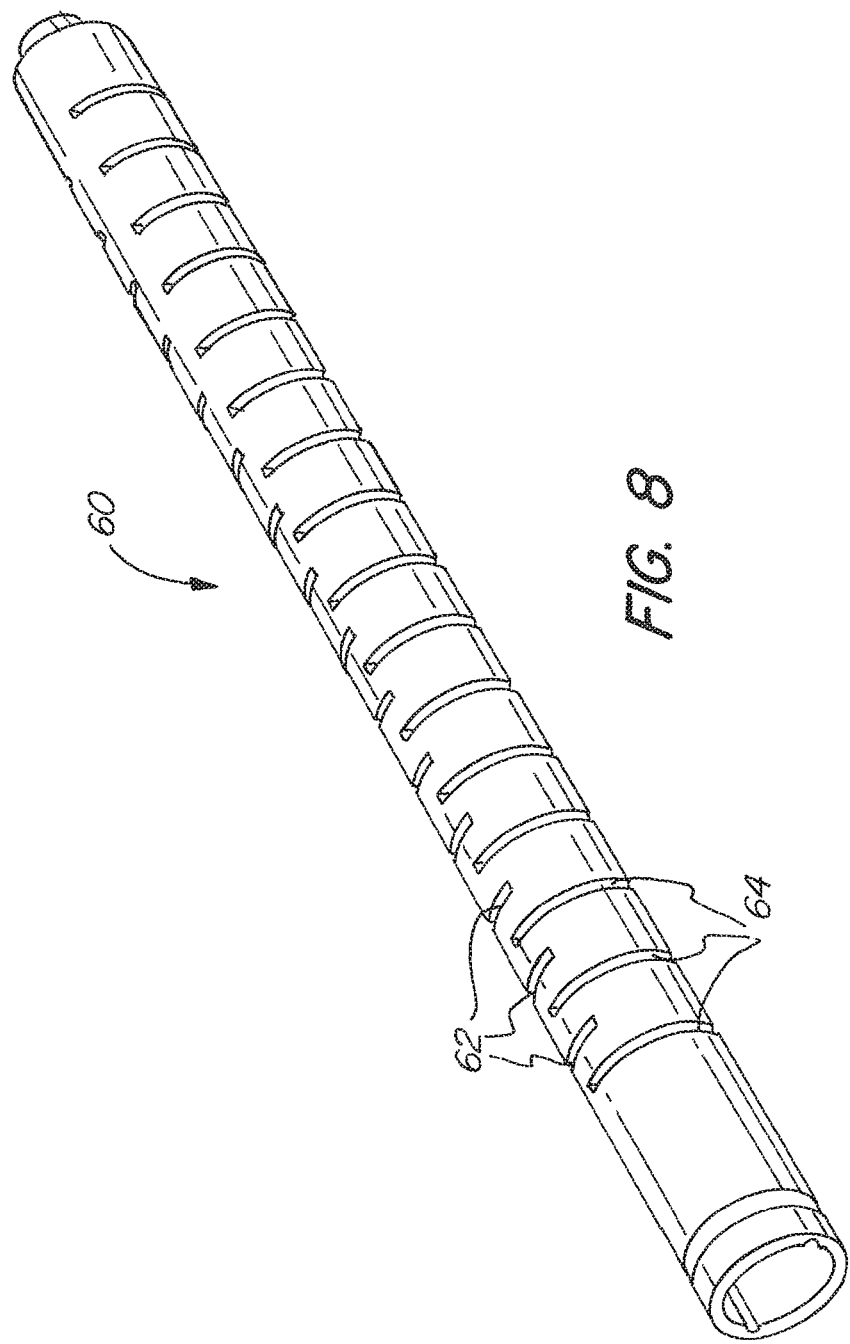
FIG. 8 is a perspective view of the flexing tip member of the catheter device of FIG. 1, with slits having different arc lengths.
Figure 12:
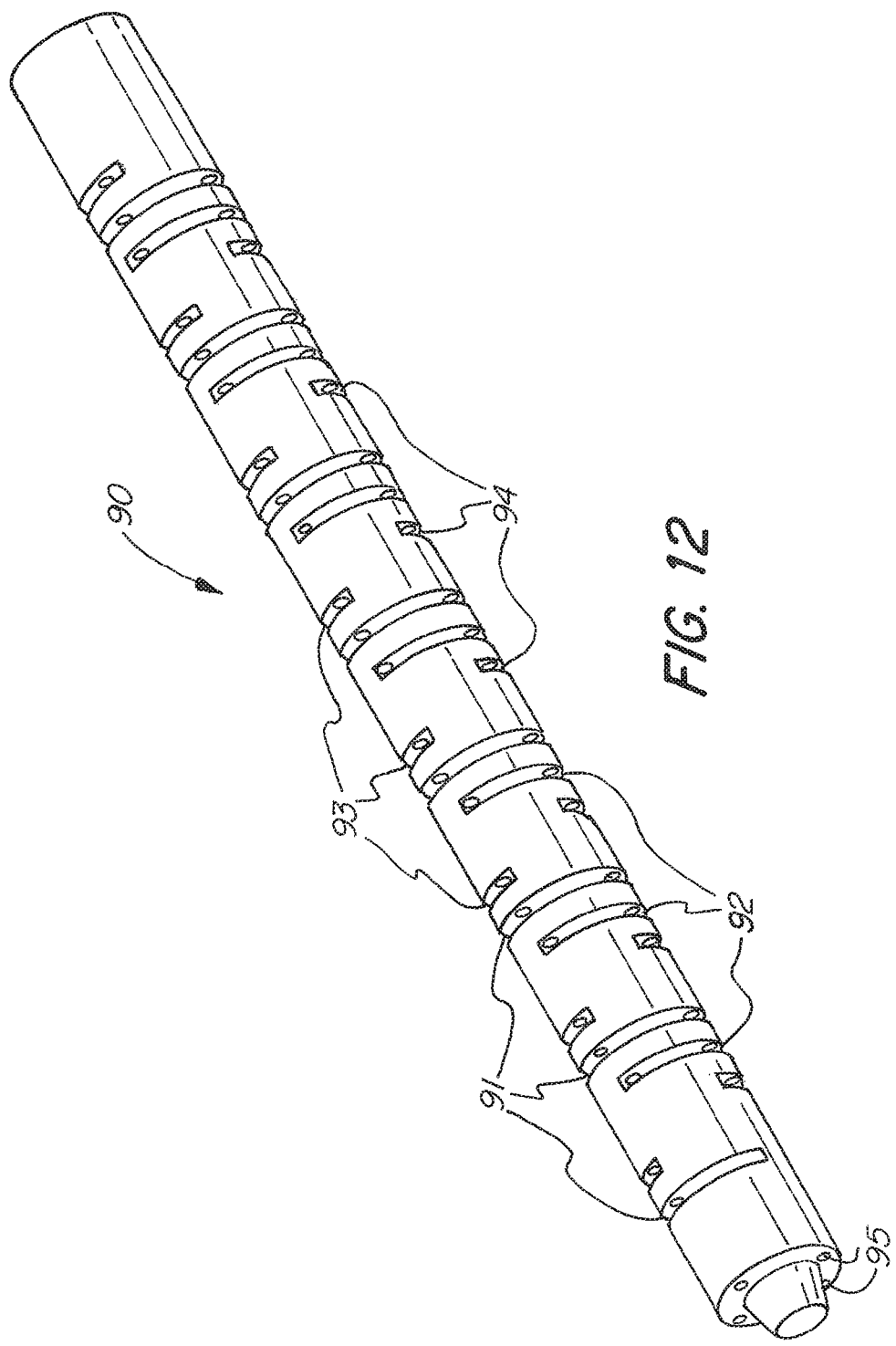
FIG. 12 is a perspective view of the flexing tip member of the catheter device of FIG. 1, having four sets of slits.

In this embodiment of the flexing tip member, an arc length of the first plurality of slits (62) and the second plurality of slits (64) gradually changes along the length of the flexing tip member (60). As shown in FIGS. 9B-9D, some of the first and second pluralities of slits (62, 64) have an arc length (70) greater than 180 degrees, some have an arc length (72) of about 180 degrees, and some have an arc length (74) of less than 180 degrees. In some embodiments, the length of the slit arcs may be changed gradually, as shown in FIG. 8. In other embodiments, the flexing tip member may have separate sections, wherein each of the sections has slits with the same arc length, but the arc length of the slits in one section is different from the arc length of the slits in another section. The arc length may be continuously decreased or increased from the proximal to the distal end of the flexing tip member, or may be repeatedly increased and decreased along the length of the tip member. These various embodiments of the flexing tip member allow for a desired variation in the bending characteristic of the catheter device. For example, in the embodiment shown in FIG. 8, by decreasing the arc length of the slits in a proximal direction, the distal portion of the flexing tip member will have higher flexibility and will bend easier and faster than the proximal portion of the tip member, which may be desirable for more precise maneuverability of the catheter in tight bodily spaces.

FIGS. 10 and 11A-11C illustrate another exemplary embodiment of the flexing tip member. The flexing tip member (80) includes a first plurality of arcuate slits (82) and a second plurality of arcuate slits (84). The first and second pluralities of slits (82, 84) are diametrically opposed, and the first plurality of slits (82) alternate with the second plurality of slits (84). Each of the slits has two ends (88) and a center (87) and an arc length extending between the two ends of each slit. In this embodiment, as seen in FIGS. 11B-11C, all of the arcs have a length (89) of more than 180 degrees. All of the first plurality of slits (82) have their centers positioned along a first axis substantially parallel to the longitudinal axis of the catheter body, and all of the second plurality of slits (84) have their centers positioned along a second axis substantially parallel to the longitudinal axis of the catheter body.

In this embodiment of the flexing tip member, a distance (86) between each pair of adjacent slits changes along the length of the flexing tip member (80), as illustrated in FIG. 10, but a distance (83) between the adjacent slits within each pair remains the same. It is understood that in other embodiments, both the distance (86) between each pair of adjacent slits, as well as the distance (83) between the adjacent slits within each pair, may be changed along the length of the flexing tip member.

In some embodiments, the distance between the adjacent slits may change gradually, as shown in FIG. 10. In other embodiments, the flexing tip member may have separate sections, wherein in each of the sections, the distance between the adjacent slits is the same, but is different from the distance in other sections. The distance between the slits may be continuously decreased or increased from the proximal to the distal end of the flexing tip member, or may be repeatedly increased and decreased along the length of the tip member. Similarly to the embodiments of the flexing tip member described above, these variations in the configuration and positioning of the slits allow for a desired variation in the bending characteristic of the catheter device.

Yet another exemplary embodiment of the flexing tip member of the present invention is illustrated in FIGS. 12-15. The flexing tip member (90) has a first plurality of arcuate slits (91), a second plurality of arcuate slits (94), a third plurality of arcuate slits (93) and a fourth plurality of arcuate slits (92). The first and second pluralities of slits (91, 94) are diametrically opposed, and the first plurality of slits (91) alternate with the second plurality of slits (94). Similarly, the third plurality of arcuate slits (93) and the fourth plurality of arcuate slits (92) diametrically opposed and the third plurality of arcuate slits (93) alternates with the fourth plurality of arcuate slits (92).

As shown in FIGS. 14B-14E, each of the first, second, third and fourth pluralities of slits (91, 94, 93, 92) has two ends (97, 101, 99, and 95 respectively) and a center (98, 102, 100, and 96 respectively) positioned midway between the two ends. All of the first, second, third and fourth pluralities of slits (91, 94, 93, 92) have an arc length (104, 106, 105, and 103 respectively) of more than 180 degrees. However, it is understood that in other embodiments, the arc length may vary between the first, second, third and fourth pluralities of slits, or may vary within each of the pluralities of slits. The arc length may increase or decrease gradually, or the flexing tip member may have sections with the same arc length, but the arc length may differ between the sections. In additional embodiments, the arc length may change continuously, or may change repeatedly along the length of the flexing tip member.

Figure 13:
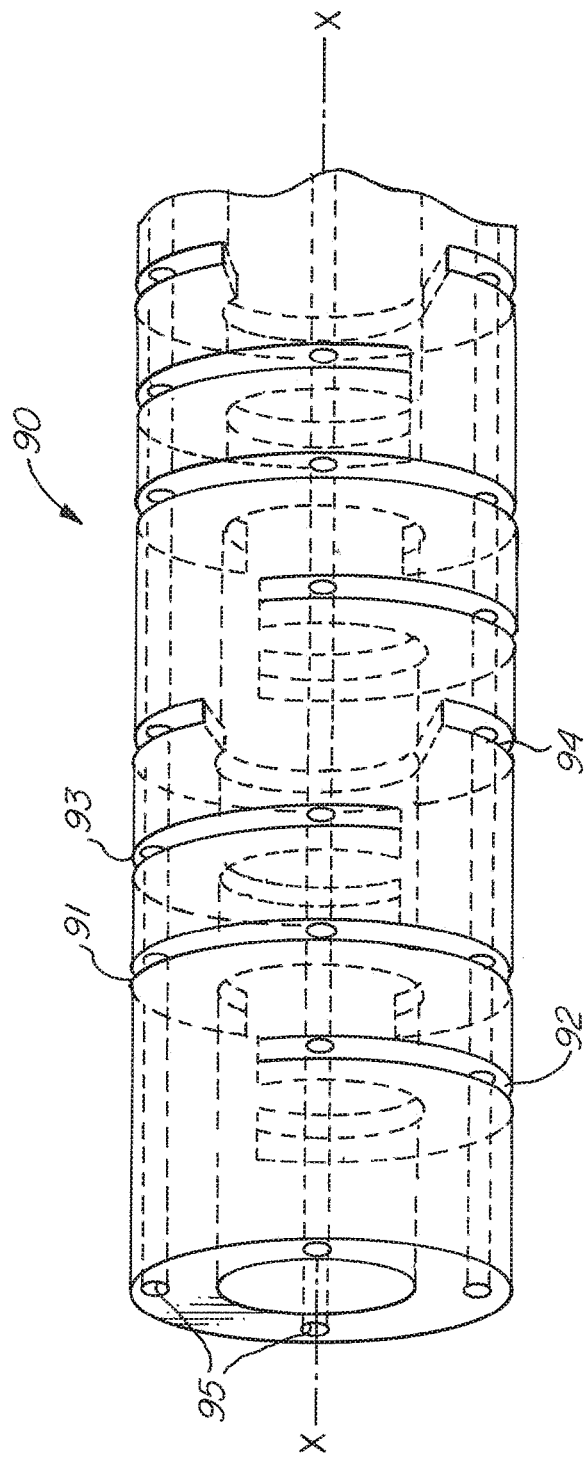
FIG. 13 is a partially schematic perspective view of the flexing tip member of FIG. 12.

As illustrated in FIG. 13, all of the first plurality of slits (91) have their centers (98) positioned along a first axis substantially parallel to the longitudinal axis (X-X) of the catheter body, and all of the second plurality of slits (94) have their centers (102) positioned along a second axis substantially parallel to the longitudinal axis of the catheter body. Furthermore, all of the third plurality of arcuate slits (93) have their centers (100) positioned along a third axis substantially parallel to the longitudinal axis of the catheter body and radially offset at approximately a 90 degree angle from the first axis, and all of the fourth plurality of arcuate slits (92) have their centers (96) positioned along a fourth axis substantially parallel to the longitudinal axis of the catheter body and radially offset at approximately a 90 degree angle from the second axis.

This embodiment of the flexing tip member allows the member to bend in two different planes, as shown in FIG. 15. The flexing tip member is provided with four channels (95) that accommodate four pull cables (107, 108) coupled to the actuator provided at the proximal end of the catheter device. Each of the channels is radially offset from the adjacent channels by about 90 degrees. Actuation of a first pair (107) of the diametrically opposed cables allows for bending of the flexing tip member in a first plane, and actuation of a second pair (108) of the diametrically opposed cables provides for bending of the flexible tip member in a second plane. The first and second planes may be substantially parallel to the longitudinal axis of the catheter body and may be substantially perpendicular to one another. This design allows for an increased maneuverability of the catheter device.

The catheter device (10) of the present invention further includes an imaging device. In the embodiment illustrated in FIG. 1, the imaging device (23) is coupled to the distal end of the flexing tip member (20). However, it is understood that in other embodiments, the imaging device may be movably disposed in the inner lumen of the catheter body (12) and the flexing tip member (20). The imaging device can be any known imaging device suitable for viewing the target area, such as a coherent fiber bundle or appropriate optical element and lens assembly in conjunction with an imaging sensor (e.g., CMOS, CCD), having a sufficiently small outer diameter, preferably about 0.75 mm-1.5 mm, and more preferably about 1 mm or less.

Figure 16B:
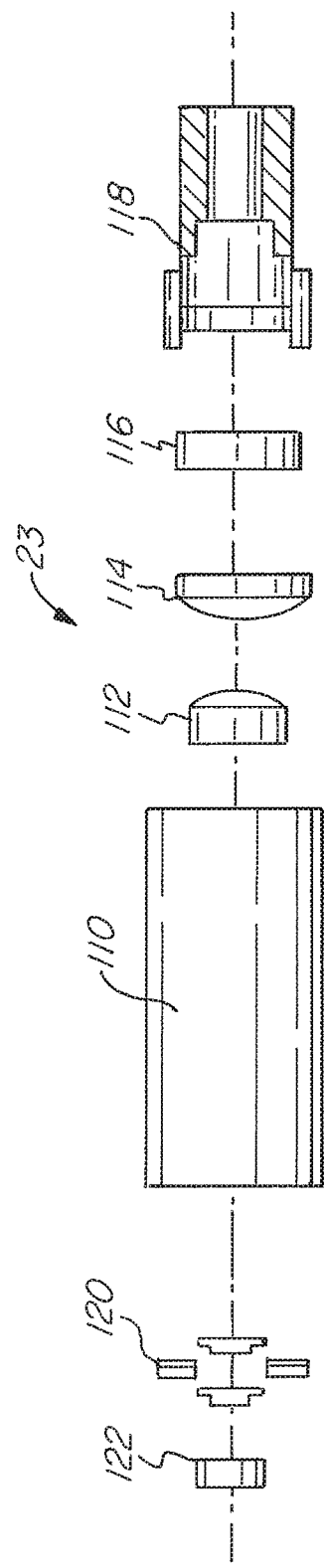
FIG. 16B is an exploded side view of an imaging device of the catheter device of FIG. 1.

One advantageous embodiment of the imaging device is illustrated in FIGS. 16A and 16B. The imaging device (23) includes a housing (110) that houses all components of the imaging device. The housing (110) is made with any suitable material, such as plastic or metal, and has any desired shape and size. The imaging device (23) also includes one or more lens positioned in the housing. In the embodiment shown in these figures, the imaging device (23) includes two positive lenses, such as plano-convex lenses (112) and (114) positioned opposite of each other such that the convex sides of the lenses are facing each other. It is understood that any other lens type and arrangement may be used in accordance with the present invention, as desired.

The imaging device (23) further includes an imaging sensor (116) positioned proximally from the lens (112) and (114). Any type of imaging sensor may be used. The imaging sensor (116) is coupled to a sensor mount (118) to position the sensor inside the housing (110). In one advantageous embodiment, a CMOS sensor is used. The housing (110) also has one or more illumination devices (120), e.g. LEDs, positioned distally from the lens. It is understood than other types of illumination devices may be used. A distal end of the housing (110) has a cover glass (122) that seals the distal end of the housing to protect the components of the imaging device positioned in the housing.

The imaging device may be oriented substantially parallel to the longitudinal axis of the catheter body. In other advantageous embodiments shown in FIGS. 17A and 17B, the imaging device (23) may be positioned at a certain angle to the longitudinal axis of the catheter body. Such design allows for better imaging of anatomy of the bodily cavities or medical instrument cavities located above the imaging device. In further embodiments, the imaging device may be tilted to different angles while being operated depending on the desired angle of view.

Figure 18:
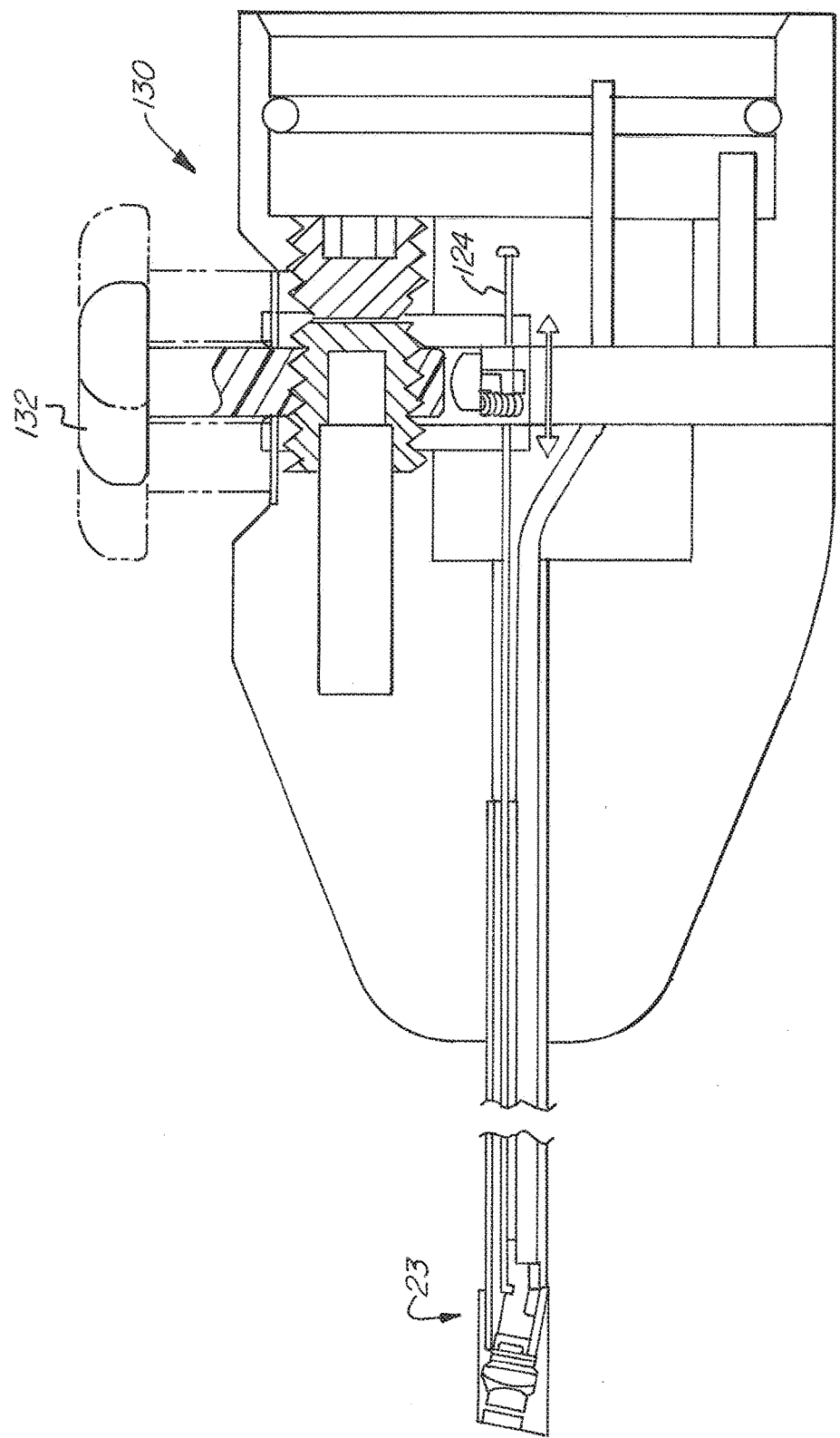
FIG. 18 is an enlarged cross-sectional view of the proximal end of the catheter device of FIG. 1, showing an actuator for the imaging device.

In the embodiment illustrated in FIGS. 17A-17B and 18, the imaging device (23) further includes an actuator that enables movement of the imaging sensor (116) towards and away from the lens (114). Any suitable actuator may be used in accordance with the present invention. In the embodiment shown in these figures, the actuator includes a pull wire or cable (124), a distal end of which is coupled to the sensor mount (118), and a proximal end of which is coupled to the actuator member (130) provided at the proximal end of the catheter body. The actuator further includes a compressible spring (126) coupled to the pull cable (124). When the pull cable is coiled in a proximal direction, the sensor mount (118) with the imaging sensor (116) move in the proximal direction away from the lens (114). This causes the spring (126) to assume an elongated state under tension. Then, as the pull cable (124) is released, the spring (124) naturally comes back to its un-extended state, thereby moving the sensor mount with the sensor closer to the lens. This motion of the imaging sensor towards and away from the lens facilitates adjustment of the focus of the imaging device, especially in situations where the object being imaged is positioned at a close proximity to the imaging device.

FIG. 18 illustrates an exemplary embodiment of the actuator member (130) for actuating the imaging device (23). The actuator member (130) includes a thumb actuator (132) coupled to the pull cable (124). The thumb pull (132) slides on a track provided in the actuator member housing. The motion of the thumb pull (132) causes the pull cable (124) to move proximally and distally, which in turn moves the imaging sensor towards and away from the lens, as described above.

It is understood that the imaging device design illustrated in FIGS. 16-18 is only exemplary and that any other design may be used with the system of the present invention.

The catheter system of the present invention further includes a processor coupled to the imaging device for receiving and processing image data captured by the imaging device. Any suitable processor may be used in accordance with the present invention. For example, the processor may be a personal computer. In one advantageous embodiment, the processor is connected to the imaging device via a cable connection. In additional advantageous embodiments, the processor is connected to the imaging devices via a wireless connection, which is desirable if a physician is located remotely from a patient being examiner or treated. Furthermore, the imaging device and/or the processor may be connected to an external storage device. The image data captured by the imaging device is stored on the storage device and may be later retrieved by a user. In other advantageous embodiments, the processor may have an internal storage device. Any suitable storage device may be used in accordance with the present invention.

The catheter system may further include a display coupled to the processor via a cable connection or via a wireless connection. The display receives imaging data processed by the processor and displays the image of the person's anatomy to a physician. Any suitable type of a display may be used in accordance with the present invention. In further advantageous embodiments, the catheter system further includes a user interface coupled to the processor. The user interface may be a graphical user interface (GUI), a keyboard, or any other suitable device that allows a user to input information and commands. The user interface is connected to the processor via a cable connection or via a wireless connection, and may be displayed on the display as on overlay image.

Figure 19:
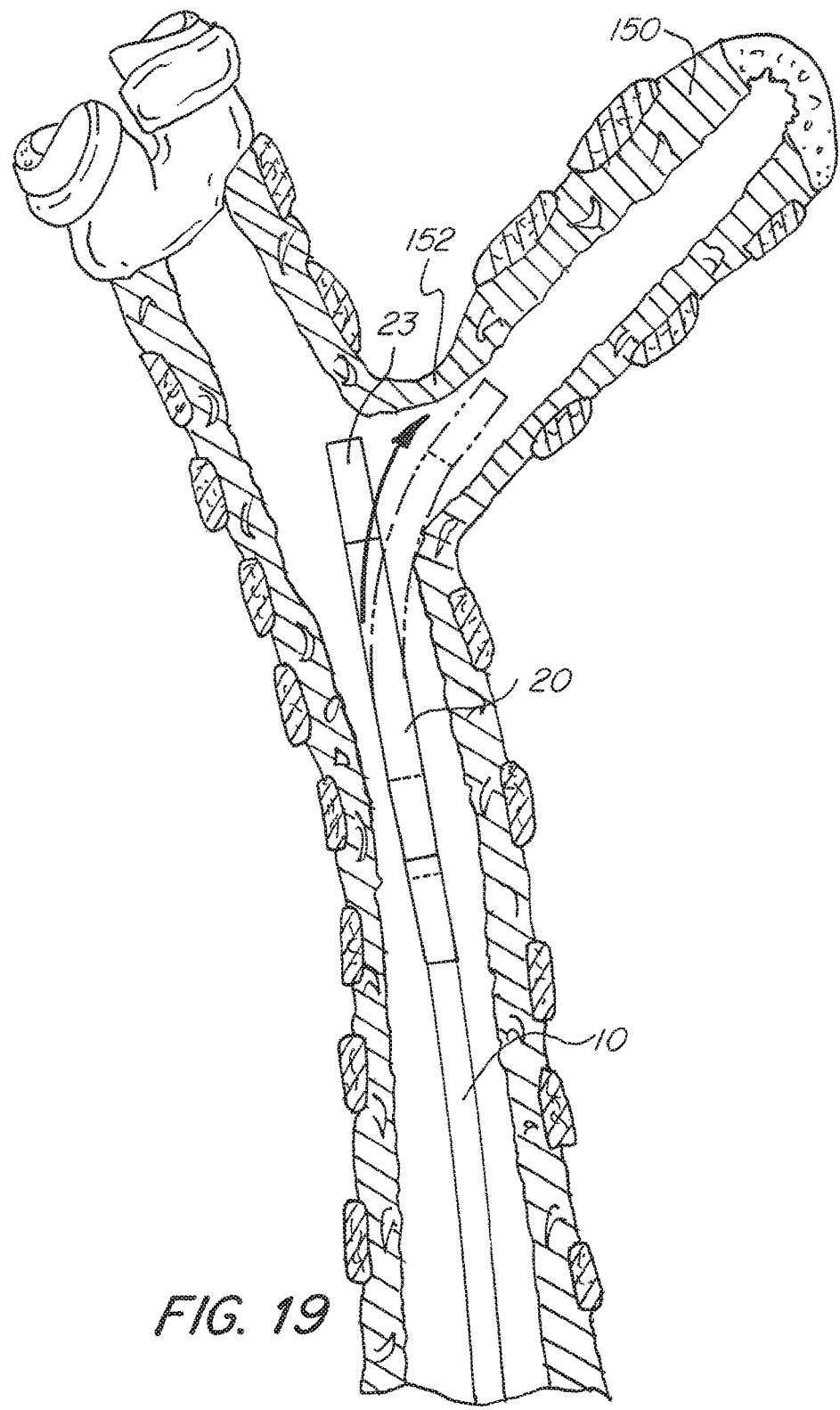
FIG. 19 is a cross-sectional view of a bodily cavity, showing the catheter device of FIG. 1 being inserted into the bodily cavity.

FIG. 19 illustrates operation of the catheter device (10) of the present invention inside a bodily cavity (150). The catheter device is inserted into the bodily cavity via a surgical incision or a natural orifice and is then guided through the cavity (150). The maneuvering of the catheter inside the cavity is facilitated by the imaging device (23) positioned at the distal end of the catheter body. When the distal end of the catheter encounters a body cavity wall (152), the flexing tip member (20) positioned at the distal portion of the catheter is bent to a desired degree to avoid the cavity wall such that the catheter may be advanced further into the cavity (150).

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A steerable, medical catheter device for insertion into a bodily cavity, comprising:
   a catheter body having a proximal end, a distal end and a longitudinal axis;
   a flexing tip member separate from the catheter body and coupled to the distal end of said catheter body and having a length, wherein said flexing tip member comprises a wall with a first plurality of arcuate slits and a second plurality of arcuate slits, wherein said first plurality of slits and said second plurality of slits are diametrically opposed, and wherein said first plurality of slits alternate with said second plurality of slits;
   a wrap covering the separate flexing tip member, wherein the wrap can be removed such that the flexing tip member can be disconnected from the catheter body; and
   an actuator that bends said flexing tip member;
   wherein at least a portion of said catheter body comprises a braided sheath; and
   wherein each of said first and second plurality of slits has two ends and a center positioned midway between the two ends and wherein all of said first plurality of slits have centers positioned along a first axis substantially parallel to the longitudinal axis of the catheter body and all of said second plurality of slits have centers positioned along a second axis substantially parallel to the longitudinal axis of the catheter body; and
   wherein each of said first and second plurality of arcuate slits is substantially straight along an entire length of the arcuate slit.

2. The catheter device of claim 1, wherein said slits are cut through the wall of said flexing tip member in a plane substantially perpendicular to the longitudinal axis of said catheter body.

3. The catheter device of claim 1, wherein each of said first plurality of arcuate slits and each of said second plurality of arcuate slit have an arc length greater than 180 degrees.

4. The catheter device of claim 1, wherein an arc length of said first plurality of slits and said second plurality of slits gradually changes along the length of said flexing tip member.

5. The catheter device of claim 4, wherein said flexing tip member comprises:
   a first section, in which each of said first plurality of arcuate slits and each of said second plurality of arcuate slits has an arc length greater than 180 degrees;
   a second section, in which each of said first plurality of arcuate slits and each of said second plurality of arcuate slits has an arc length of about 180 degrees; and
   a third section, in which each of said first plurality of arcuate slits and each of said second plurality of arcuate slits has an arc length less than 180 degrees.

6. The catheter device of claim 1, wherein a distance between adjacent slits is the same along the length of said flexing tip member.

7. The catheter device of claim 1, wherein a distance between adjacent slits changes along the length of said flexing tip member.

8. The catheter device of claim 1, wherein said actuator comprises at least two pull cables extending through the wall of said flexing tip member.

9. The catheter device of claim 8, wherein said imaging device is movably disposed in an inner lumen of said flexing tip member.

10. The catheter device of claim 8, wherein said imaging device is coupled to a distal end of said flexing tip member.

11. The catheter device of claim 10, wherein said imaging device comprises:
a housing;
at least one imaging sensor positioned in the housing;
at least one lens positioned distally from said at least one imaging sensor; and
at least one illumination device positioned adjacent said at least one imaging sensor.

12. The catheter device of claim 11, wherein said imaging device further comprises an actuator that moves said at least one imaging sensor relative said at least one lens.

13. The catheter device of claim 11, wherein said imaging sensor comprises a CMOS sensor.

14. The catheter device of claim 13, wherein said at least one lens comprises at least one positive lens.

15. The catheter device of claim 14, wherein said at least one lens comprises two piano-convex lenses positioned distally from said imaging sensor.

16. The catheter device of claim 11, wherein said illumination device comprises a LED.

17. The catheter device of claim 1, further comprising an imaging device.

18. The catheter device of claim 1, wherein the wall of said flexing tip member further comprises a third plurality of arcuate slits and a fourth plurality of arcuate slits, wherein said third plurality of arcuate slits and said fourth plurality of arcuate slits are diametrically opposed, wherein said third plurality of arcuate slits alternate with said fourth plurality of arcuate slits, and wherein each of said third and fourth plurality of arcuate slits has two ends and a center positioned midway between the two ends, and wherein all of said third plurality of arcuate slits have centers positioned along a third axis substantially parallel to the longitudinal axis of the catheter body and radially offset at approximately 90 degree angle from said first axis, and all of said fourth plurality of arcuate slits have centers positioned along a fourth axis substantially parallel to the longitudinal axis of the catheter body and radially offset at approximately 90 degree angle from said second axis.

19. The catheter device of claim 1, further comprising:
an imaging device having an imaging device housing coupled to a distal end of the flexing tip member;
a sensor mount disposed in the imaging device housing;
an imaging sensor mounted to the sensor mount in the imaging device housing;
a lens positioned in the imaging device housing distal to the imaging sensor;
a pull wire having a distal end coupled to the sensor mount;
an actuator coupled to a proximal end of the pull wire, such that the actuator adjusts the focus of the imaging device by moving the imaging sensor away from the lens by pulling the sensor mount in a proximal direction and moving the imaging sensor towards the lens by pushing the sensor mount in a distal direction.

20. The catheter device of claim 19, wherein the actuator includes a compressible spring coupled to the pull wire such that, when the actuator pulls the sensor mount in the proximal direction via the pull wire, the spring assumes an elongated state under tension, and when the pull wire is released, the spring returns to an unextended state, thereby moving the sensor mount in the distal direction.

21. A steerable, medical catheter device for insertion into a bodily cavity, comprising:
a catheter body having a proximal end, a distal end and a longitudinal axis;
a flexing tip member separate from the catheter body and coupled to the distal end of said catheter body and having a length, wherein said flexing tip member comprises a wall with a first plurality of arcuate slits and a second plurality of arcuate slits, wherein said first and second plurality of slits are diametrically opposed, and wherein said first plurality of slits alternate with said second plurality of slits;
a wrap covering the separate flexing tip member, wherein the wrap can be removed such that the flexing tip member can be disconnected from the catheter body;
an actuator that bends said flexing tip member, wherein said actuator comprises at least two pull cables extending through the wall of said flexing tip member; and
an imaging device coupled to a distal end of said flexing tip member;
wherein at least a portion of said catheter body comprises a braided sheath; and
wherein each of said first and second plurality of arcuate slits is substantially straight along an entire length of the arcuate slit.

22. The catheter device of claim 21, wherein each of said first and second plurality of slits has two ends and a center positioned midway between the two ends, and wherein all of said first plurality of slits have centers positioned along a first axis substantially parallel to the longitudinal axis of the catheter body and all of said second plurality of slits have centers positioned along a second axis substantially parallel to the longitudinal axis of the catheter body.

23. The catheter device of claim 21, wherein said imaging device comprises:
a housing;
at least one imaging sensor positioned in the housing;
at least one lens positioned distally from said at least one imaging sensor; and
at least one illumination device positioned adjacent said at least one imaging sensor.

24. The catheter device of claim 23, wherein said imaging device further comprises an actuator that moves said at least one imaging sensor relative said at least one lens.

25. The catheter device of claim 23, wherein said imaging sensor comprises a CMOS sensor.

26. The catheter device of claim 23, wherein said at least one lens comprises at least one positive lens.

27. The catheter device of claim 26, wherein said at least one lens comprises two piano-convex lenses positioned distally from said imaging sensor.

28. The catheter device of claim 23, wherein said illumination device comprises a LED.

* * * * *